United States Patent [19]
Paul

[11] Patent Number: 5,782,409
[45] Date of Patent: *Jul. 21, 1998

[54] AIR FRESHENING AND DEODORIZING SYSTEM

[76] Inventor: Leonard Paul, 13 Stuart Dr., Bloomfield, Conn. 06002

[*] Notice: The term of this patent shall not extend beyond the expiration date of Pat. No. 5,372,303.

[21] Appl. No.: 670,499

[22] Filed: Jun. 27, 1996

Related U.S. Application Data

[63] Continuation-in-part of Ser. No. 418,079, Apr. 6, 1995, Pat. No. 5,611,486, which is a continuation-in-part of Ser. No. 333,027, Nov. 1, 1994, Pat. No. 5,556,030, which is a continuation-in-part of Ser. No. 163,338, Dec. 6, 1993, Pat. No. 5,372,303.

[51] Int. Cl.$^6$ .................................................... A61L 9/12
[52] U.S. Cl. ................... 239/56; 239/58; 428/905
[58] Field of Search .................... 239/34, 44, 49, 239/51.5, 53–58, 60; 428/905

[56] References Cited

U.S. PATENT DOCUMENTS

| | | | |
|---|---|---|---|
| 2,626,833 | 1/1953 | Valentine | 239/56 |
| 4,529,125 | 7/1985 | Sullivan | 239/56 |
| 4,712,737 | 12/1987 | Hecking | 239/58 |
| 4,958,768 | 9/1990 | Ishihara | 239/34 |
| 5,164,178 | 11/1992 | Muysson | 239/60 X |

*Primary Examiner*—Lesley D. Morris
*Attorney, Agent, or Firm*—Melvin I. Stoltz

[57] ABSTRACT

By securely sealing odor absorbing material and fragrance producing compositions separately in a flexible container, preferably formed from multi-layered sheet material, a unique and highly desirable air freshening and deodorizing system is attained. In the preferred embodiment, the odor absorbing material is retained by at least one microporous or permeable membrane to prevent unwanted dispersion of the odor absorbing material into the ambient surroundings, while also controlling the rate of transfer of the ambient air into contact with the odor absorbing material. In addition, fragrance producing compositions are incorporated into the container to provide the desired fragrance simultaneously with the absorption of odors from the ambient surroundings. Preferably, the air freshening and deodorizing system of this invention employs a small, compact and flexibly moldable container or housing which enables the system to be easily positioned in any desired location, regardless of the size constraints imposed thereon.

27 Claims, 7 Drawing Sheets

FIG. 1
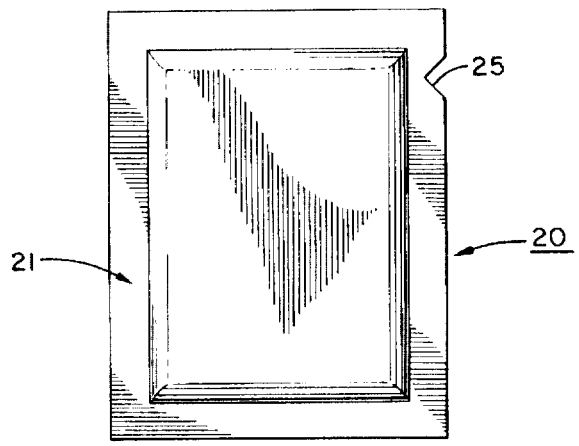
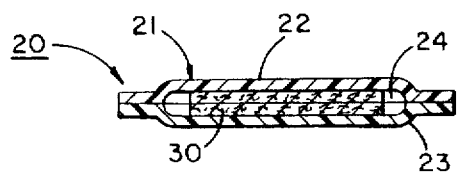
FIG. 2
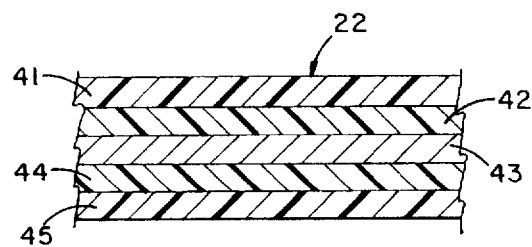
FIG. 3
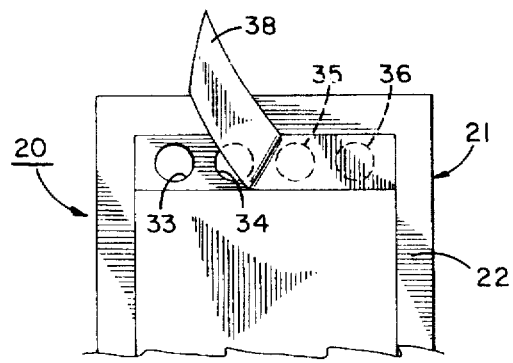
FIG. 4

5,782,409

AIR FRESHENING AND DEODORIZING SYSTEM

This application is a continuation-in-part application of U.S. Ser. No. 08/418,079, filed Apr. 6, 1995, now U.S. Pat. No. 5,611,486, which issued Mar. 18, 1997; which is a continuation-in-part of U.S. Ser. No. 08/333,027, filed Nov. 1, 1994, now U.S. Pat. No. 5,556,030 which issued on Sep. 19, 1996; which is a continuation-in-part of U.S. Ser. No. 08/163,338, filed Dec. 6, 1993, now U.S. Pat. No. 5,372,303, issued Dec. 13, 1994.

TECHNICAL FIELD

This invention relates to air fresheners and/or deodorizers and, more particularly, to an integrated system for containing and dispensing the desired air freshening/deodorizing fragrances or odor absorbing materials.

BACKGROUND ART

Air freshening or deodorizing has long been sought by consumers, in both residential and commercial environments. Due to the wide variety of odors which are generated, the desire to reduce or eliminate offensive odors has long existed along with the desire to provide a long-lasting pleasing odor.

In an attempt to meet the demand for air fresheners or deodorizers, numerous products have been developed and are presently available in the marketplace. In general, these prior art products are sold as solids, liquids, or aerosol sprays to provide the desired air freshening or deodorizing effect. Typically, these prior art products are used to eliminate, chemically change, or mask an existing odor. In addition, these products typically work by absorbing odorous molecules, dissolving or emulsifying such molecules, or killing bacteria that causes the offensive odor.

Although substantial effort has been expended in providing various delivery systems for establishing a pleasant odor in areas or environments in which offensive odors continuously exist, no fully satisfactory delivery system has been attained which is capable of providing long-term deodorizing or air freshening. In particular, such prior art systems as spray deodorants are capable of providing only temporary relief in freshening the air or eliminating the undesirable odors. Once the product has been sprayed into the air, the odor-changing spray quickly dissipates, providing only temporary or transitory relief. This limited benefit is particularly true in environments where heating or cooling is provided by forced air flow, since the air flow further increases air turbulence, causing the air freshening spray to dissipate more rapidly.

Similar short term beneficial effects are also attained with the liquid and solid air freshening products which are capable of only providing limited distribution of the deodorizer or air freshener and often become depleted of any beneficial effect over a short duration. Consequently, these products have only been capable of realizing limited acceptance and use.

Prior art systems typically range from simple dispensers containing the air freshening material to more complex, delivery systems constructed for decorative or designer effects. Unfortunately, such decorative effects cause such products to be substantially more expensive, with the ability of these products to deliver long-term continuous air freshening or deodorizing not being enhanced.

One prior art system employs a multi-layered flexible package for use in association with vacuum cleaners in order to provide air freshening or deodorizing during the vacuuming operation. However, these products are typically not capable of being employed in other environments and are unable to provide long-lasting, continuous, dependable air freshening or deodorizing due to the use of sponge material as the fragrance carrier. As a result, these prior art products lacked versatility and broad-based usability.

Another prior art system attempts to achieve greater fragrance distribution by using electricity to heat the dispenser. Although greater fragrance distribution is attained over solid, non-heated dispensers, these prior art systems are extremely expensive and provide only a very limited, moderate improvement.

Therefore, it is a principal object of the present invention to provide a fully integrated, air freshening and/or deodorizing system which provides a highly concentrated, readily dispersible air freshening/deodorizing composition which is capable of providing long-term, delivery of the desired fragrance.

Another object of the present invention is to provide an air freshening/deodorizing system having the characteristic features described above which provides a fully integrated, leak-free container system with a fragrance holding and dispersing system which assures continuous, complete and controlled dispersion of the fragrance only when desired by the user.

Another object of the present invention is to provide an air freshening/deodorizing system having the characteristic features described above which incorporates odor absorbing material which removes unwanted odors from the ambient air in order to provide the desired air freshening or deodorizing.

Another object of the present invention is to provide an air freshening/deodorizing system having the characteristic features described above which is capable of providing an easily employable, variable opening system for enabling the user to control the amount of fragrance being dispersed.

Another object of the present invention is to provide an air freshening/deodorizing system having the characteristic features described above which is capable of being easily positioned in a wide variety of locations, previously unattainable, due to the overall construction of the system of the present invention.

A further object of the present invention is to provide an air freshening/deodorizing system having the characteristic features described above which is capable of being easily employed in both residential and commercial establishments for providing long-term air freshening and/or deodorizing throughout the entire building or zone within which the system is employed.

Another object of the present invention is to provide an air freshening/deodorizing system having the characteristic features described above which is a easily employed in air conditioning and heating ducts or other heat delivering systems.

Another object of the present invention is to provide an air freshening/deodorizing system having the characteristic features described above which is safe for use with children as well as constructed in a system which virtually eliminates any possibility of unwanted use or contact by children.

Another object of the present invention is to provide an air freshening/deodorizing system having the characteristic features described above which is able to cooperate with all conventional heating and cooling systems to circulate the desired fragrance or the ambient air without requiring mounted engagement with electrical outlets.

Other and more specific objects will be in part be obvious and will in part appear hereinafter.

SUMMARY OF THE INVENTION

The present invention overcomes all of the difficulties and drawbacks of prior art systems by providing a unique air freshening and/or deodorizing system. In one embodiment, the system comprises a highly concentrated, oil-based solution of the desired fragrance associated with a highly or super absorbent wicking member which is contained in a small, compact, multi-layered flexible package. In an alternate embodiment, odor absorbing material is retained in the multi-layered flexible package. The multi-layered, flexible housing or container employed as part of the system of the present invention is completely flexible and moldable into virtually any desired configuration. In this way, the system is capable of being positioned in virtually any desired location, regardless of size constraints.

Another feature of the present invention is the attainment of an air freshening/deodorizing system which is completely sealed prior to actual use and is constructed with a housing or container which is virtually impervious to the air freshening/deodorizing composition incorporated therein. Consequently, prior to user-initiated, controlled opening of the dispensing system, the contents are maintained completely sealed within the container, incapable of being released or used until desired. As a result, each package of the system is capable of being stored for virtually any desired period of time with assurance that the product will possess all of the desired air freshening/deodorizing capabilities whenever the package is opened for use.

Another feature of the present invention is the construction of the air freshening/deodorizing system which enables the user to control the size of the portal or opening in the housing through which the fragrance or ambient air passes. In this way, depending upon the amount of air freshening or deodorizing desired by the user, the housing or container can be opened minimally or completely in order to regulate the rate at which the fragrance is dispensed, or the ambient air is transferred from the housing or container. In this way, any desired application can be easily accommodated.

In the preferred embodiment, the flexible housing or container is constructed with a notch zone formed in a sealed zone of the housing to enable the user to open the air freshening/deodorizing system by advancing the notch into the pouch area within which the fragrance and wicking means, or the odor absorbing material, are contained. By controlling the area being opened, the desired portal size can be quickly and easily achieved.

If desired, other constructions can be employed in order to control the size of the dispensing zone. One such alternate construction, which has been found to be highly effective, is the incorporation of a plurality of apertures formed along one edge of the interior pouch or holding zone, in association with an overlying, removable, sealing strip which seals the apertures, maintaining the air freshening/deodorizing composition completely potent until use is desired. Whenever needed, the user merely removes all, or a portion of the sealing strip, exposing the desired number of apertures needed for the particular application. In this way, an alternate construction for completely controlling the amount of fragrance being dispensed is attained, as well as controlling the rate of use of the odor absorbing material.

In the preferred fragrance dispensing embodiment of the present invention, the wicking means comprises cotton material positioned in the holding zone or pouch in direct contact with the air freshening/deodorizing composition. Typically, the air freshening/deodorizing composition is fully absorbed throughout the wicking material, with any remaining supply of air freshening/deodorizing composition being pooled in one area of the holding zone with the wicking means in contact therewith. In this way, when the dispensing system is opened and a portion of the air freshening/deodorizing composition is expelled through the dispensing zone, the wicking material is continuously supplied with additional air freshening/deodorizing composition until all of the material has been absorbed into the wicking material and dispensed.

The cotton wicking means may be constructed with the cotton material either in a woven form or in a bat form. Regardless of which configuration is employed, it has been found that by using cotton, a continuous supply of the air freshening/deodorizing composition is maintained and effective and efficient dispensing of the composition is realized. In this way, the dispensing system of the present invention achieves a continuous, trouble-free, reliable air freshening and/or deodorizing of the desired ambient area.

If desired, other suitable materials can be employed for the wicking means as a substitute for the preferred cotton material. However, any other such substitute materials should possess similar absorbency and dispersion characteristics in order to provide the desired retention of the fragrance as well as the dispensing of the fragrance when desired.

In addition, the wicking means and fragrance can be constructed in a solid form or in a gel form in order to eliminate the need for a combined wicking means and fragrance composition. Although the use of the wicking means with the liquid fragrance is preferred, these alternate constructions can be employed without departing from the scope of the present invention.

Another feature of this embodiment of the present invention is the attainment of a unique composition for the fragrance solution. In the present invention, a fixative is employed with the fragrance to control the rate of dispersion of the fragrance. In this way, a longer lasting air freshener/deodorizer dispensing system is attained.

By employing this preferred construction, a dispensing system is realized which overcomes all of the prior art difficulties and provides a long-lasting, reliable air freshening and/or deodorizing delivery system. In particular, it has been found that the present invention is uniquely adapted for use in commercial as well as residential environments. In this regard, the present invention is applicable for being placed in air conditioning ducts in commercial installations for delivering air freshening and/or deodorizing to an entire building or wing to which air flow through a duct is being directed. Furthermore, due to the unique combination of elements attained by the present invention, this delivery system is able to be used in direct association with all types of heat delivering systems, as well as air conditioning and air flow systems.

In this regard, it has been found that the delivery system of the present invention is uniquely applicable to use in convalescent homes, hospitals, etc., where difficulty in delivering a continuous air freshening and/or deodorizing composition has existed. However, by merely placing of the present invention in an air conditioning duct or other air supply chamber, the desired air freshening and/or deodorizing fragrances are efficiently and effectively delivered throughout the desired building or zone.

It has also been found that by employing the unique wicking means, air freshening/deodorizing composition and multi-layered compact, flexible construction, the delivery system of the present invention can be easily positioned and effectively used in direct association with any conventional heating system in order to attain substantially improved fragrance dispersion. In addition, the dispensing system can be effectively positioned in otherwise inaccessible spaces or locations. These two assets are particularly employed by such locations as conventional heating systems such as hot water, electric, and hot air based systems.

Typically, a hot water based system employs radiators or hot water pipes which run along a wall directly adjacent a floor and wall. The hot water pipes are peripherally surrounded by a plurality of baffles or fins, with the fins covered by a metal housing. The heat from the hot water passes through the pipe to the radiator or fins and is conducted, by convection, through the radiator or housing to the room. By employing the present invention, the air freshening/deodorizing delivery system can be positioned in any desired location directly on or adjacent the radiator, the fins, or on the housing therefor to enable the deodorizing and/or air freshening fragrances to be carried with the warm air into the room. Electric heat systems employ similarly constructed fin and housing systems with which the dispensing system of the present invention can be easily employed to obtain the same efficacious results.

Furthermore, heated air and convection currents are employed by wood stoves to heat rooms, with the wood stoves typically having baffle means. With the present invention, the delivery system can be placed near a wood stove or on the baffles associated with the stove to attain the desired result. Care need be exercised to avoid the placement of the delivery system on a hot surface whose temperature would adversely affect the dispensing system.

Finally, hot air systems use ducts, conduits, and registers for controlling the flow of the hot air to heat the room or zones. In employing the present invention, the delivery system can be placed in the duct or register through which the hot air flows in order to heat the dispenser system and drive the dispersion of the fragrance into the room or zone. As a result, a substantially improved fragrance delivery is obtained, without requiring complex, expensive assemblies, such as are needed with prior art systems which are heated by being plugged into household electricity.

By providing a dispensing system which is capable of being used effectively and efficiently with all heating systems, the efficacy of the present invention is substantially enhanced. As detailed herein, the fragrance composition comprises a fixer for controlling its rate of dispersion and the container or housing of the dispensing system incorporates a plurality of intimately bonded integrally affixed layers, one of which comprises a metallic foil layer. As a result of this construction, the delivery system of the present invention is able to employ the heat produced by conventional heating systems to raise the temperature of the metal foil of the container. With this elevated temperature directly effecting the supply of the air freshening/deodorizing composition, the volatility of the composition is enhanced and a more effective delivery of the composition to the environment is realized.

In the preferred embodiment, the flexible container of the present invention is formed from two separate and independent sheets, each sheet of which is identical to the other and comprises a plurality of layers integrally bonded together to form the continuous sheet. Preferably, five separate layers are integrally bonded together, at least one layer of which comprises a metal foil layer which is bonded on both surfaces thereof to a plurality of separate layers formed from one or more compounds selected from the group consisting of polyester films, low density polyethylene films, ethylene acrylic acid copolymer films, and linear low density polyethylene films.

By employing this construction, two separate and independent multi-layer composite sheets are peripherally sealed to each other, forming an interior holding zone or pouch within which the super absorbent, cotton-based wicking material is mounted along with the air freshening/deodorizing composition. Once the wicking material and air freshening/deodorizing composition are positioned in the interior holding zone, the holding zone is completely sealed, assuring secure, leak free retention of the air freshening/deodorizing composition in the multi-layered container, as well as secure retention of the odor absorbing material in the alternate preferred embodiment.

By employing the multi-layered construction for each of the surfaces forming the sealed container, assurance is provided that the concentrated air freshener/deodorizing composition or the odor absorbing material is incapable of permeating, diffusing, or being dispensed through the wall of the container. This assures long-term storage of the air freshening/deodorizing system of the present invention. In this way, the present invention can be retained for as long as desired and, once opened, the user is assured that the concentrated air freshening/deodorizing composition contained therein has maintained its potency and is ready for providing the desired air freshening or deodorizing results.

In a further alternate embodiment of the present invention, the air freshening/deodorizing system of the present invention also incorporates at least one microporous or permeable membrane layer positioned between the fragrance bearing wicking means, or odor absorbing material, and one of the multi-layered composite sheets forming the dispensing system. If desired, two separate and independent layers of a microporous or permeable membrane can be employed with the microporous or permeable membrane layers being positioned on both sides of the fragrance bearing wicking means or the odor absorbing material.

By employing one or more layers of a microporous or permeable membrane positioned between the wicking means, or the odor absorbing material, and the multi-layered composite sheet forming the air freshening/deodorizing system of the present invention, the rate of diffusion of the fragrance from the dispensing system to the ambient air, or the transfer rate of the ambient air to the odor absorbing material can be controlled with greater precision and uniformity. By employing a microporous or permeable membrane having a porosity specifically selected for the molecular sizes of the fragrances being dispensed or the air being deodorized, the rate of diffusion of the fragrance or air through the microporous or permeable membrane can be controlled to further enhance and increase the longevity of the system of the present invention.

In this way, in the fragrance embodiment, any desired concentration level of the air freshening/deodorizing composition can be employed regardless of the potency of the fragrance, with the dispensing system being able to completely control the dispersion rate of the fragrance from the wicking material to the ambient air in a reliable, automatic, and completely repeatable manner. In addition to providing an inherently reliable product, the air freshening/deodorizing system of the present invention may be specially constructed for any particular application or method of use. Prior to the present invention, no such specially designed dispensing system was attainable.

The invention accordingly comprises the features of construction, combinations of elements and arrangements of parts which will be exemplified in the construction hereinafter set forth and the scope of the invention will be indicated in the claims.

THE DRAWINGS

For a fuller understanding of the nature and objects of the present invention, reference should be had to the following detailed description taken in connection with the accompanying drawings, in which:

FIG. 1 is a front elevation view showing the air freshener/ deodorizer dispensing system of the present invention;

FIG. 2 is a cross-sectional side elevation view of the air freshener/deodorizer dispensing system of the present invention;

FIG. 3 is a greatly enlarged, cross-sectional elevation view, partially broken away, depicting the preferred construction of the plurality of integrally bonded layers forming the side wall of the dispensing system of the present invention; and FIG. 4 is a front elevation view, partially broken away, depicting an alternate embodiment of the air freshening/ deodorizing system of the present invention.

Figure 5:
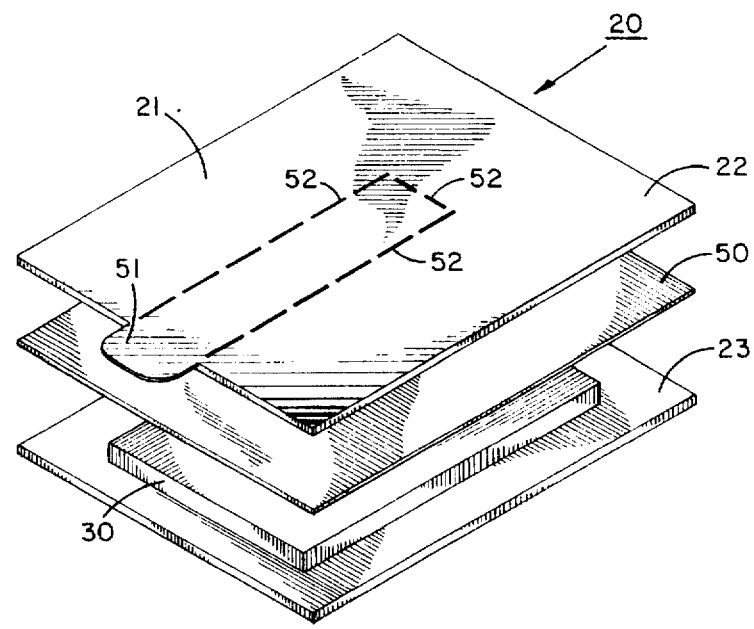
Figure 6:
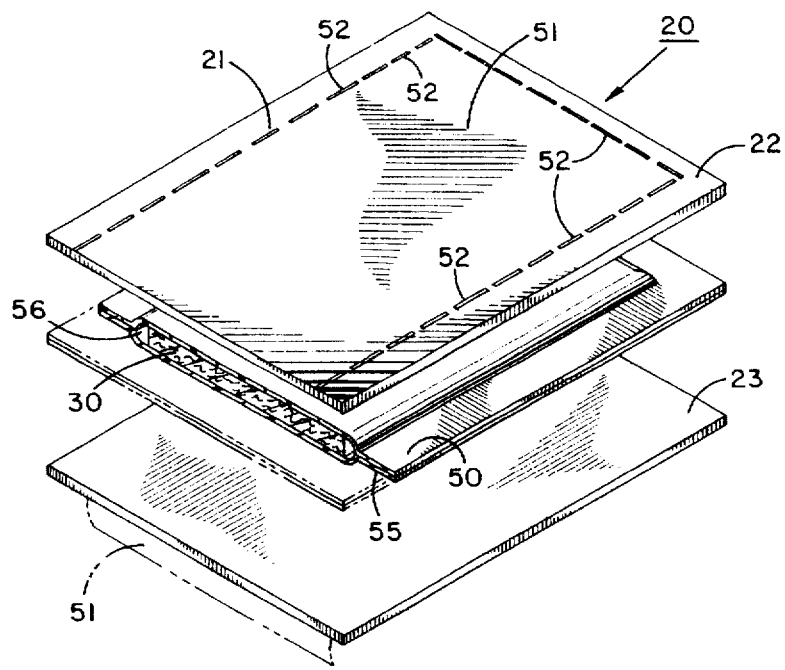
Figure 7:
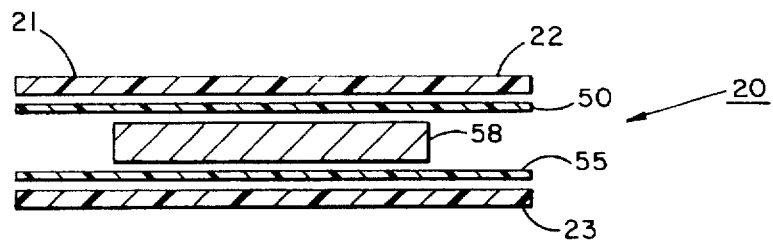
Figure 8:
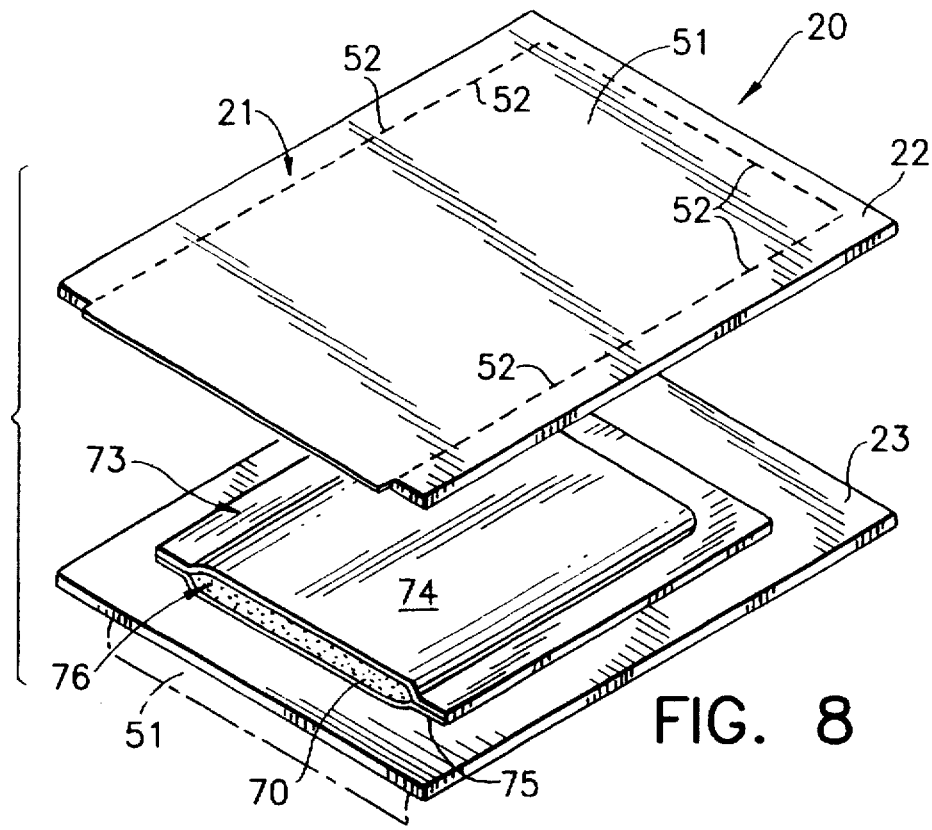
Figure 9:
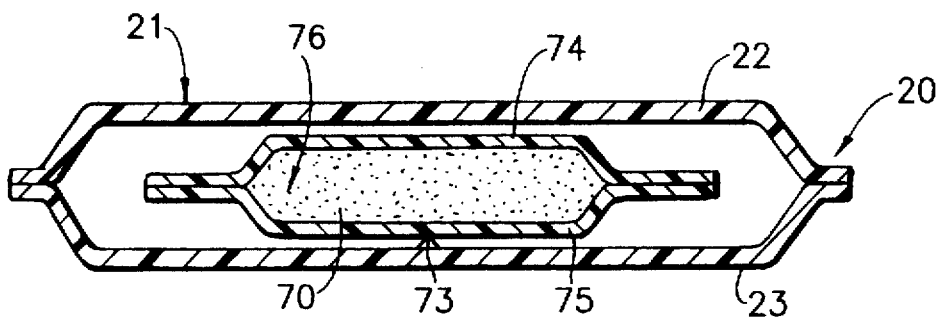

FIG. 5 is an exploded perspective view of a further alternate embodiment of the air freshening/deodorizing system of the present invention;

FIG. 6 is an exploded perspective view of a still further alternate embodiment of the air freshening/deodorizing system of the present invention;

FIG. 7 is an exploded perspective view of an additional alternate embodiment of the air freshening/deodorizing system of the present invention;

FIG. 8 is an exploded perspective view of a still further alternate embodiment of an air freshening/deodorizing system of the present invention;

FIG. 9 is a fully assembled, cross-sectional, side elevation view of the embodiment of the air freshening/deodorizing system of FIG. 8; and FIGS. 10–14 are cross-sectional side elevational views of still further alternate embodiments of the air freshening/ deodorizing system of the present invention.

Figure 15:
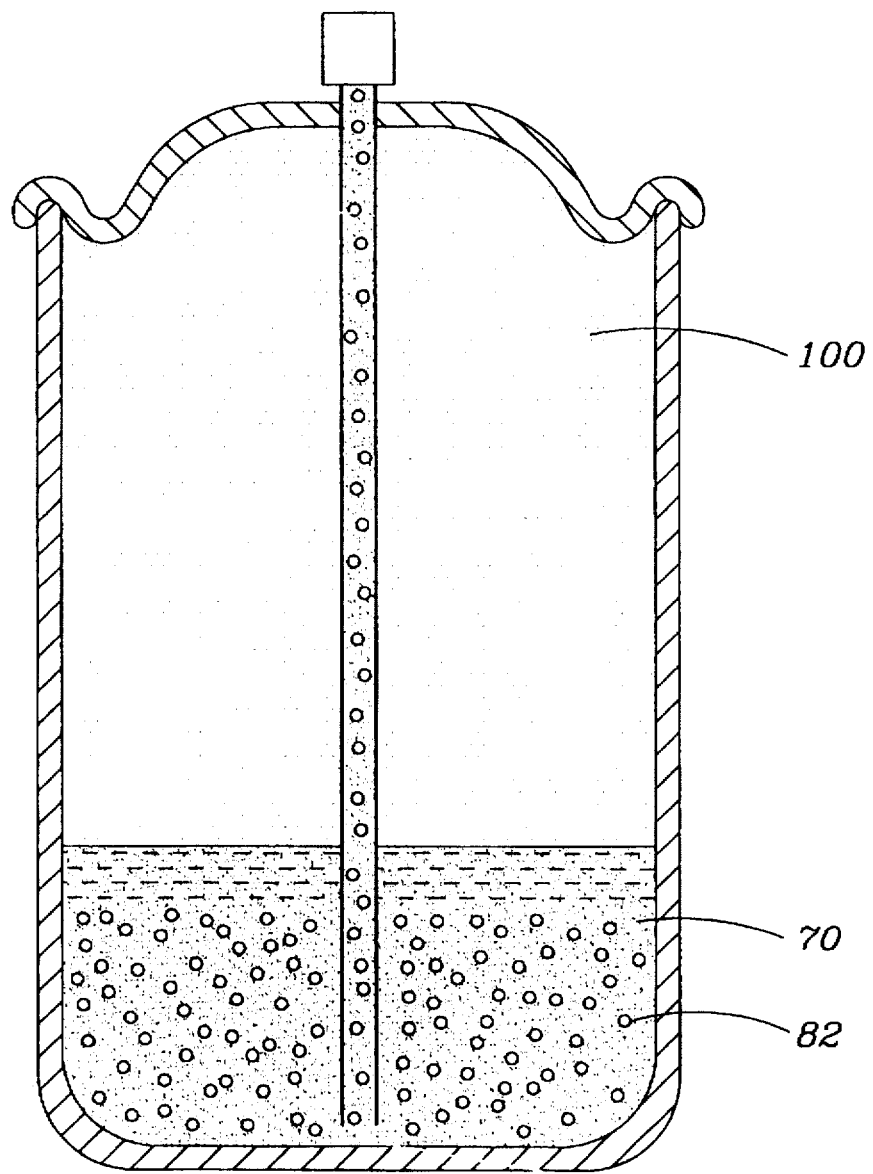

FIG. 15 is a cross-sectional view of an alternate embodiment in which the container is an aerosol spray can.

DETAILED DESCRIPTION

In FIGS. 1 and 2, the preferred embodiment of the air freshening/deodorizing system 20 of the present invention is clearly depicted. As shown therein, air freshening/ deodorizing system 20 comprises a small, compact, flexible housing or container 21 which is formed by securely affixing side walls or panels 22 and 23 to each other.

In the preferred embodiment, as fully detailed below, side walls or panels 22 and 23 each comprise a plurality of integrally bonded layers to form a high strength, nonpermeable and completely flexible panel or side wall member. In order to form container or housing 21, side walls or panels 22 and 23 are placed in overlying contacting engagement with each other and intimately bonded together about their outer peripheral edges. In this way, a completely sealed, impervious container or housing 21 is formed which is sealed about all four sides thereof and incorporates an interior holding zone or pouch 24.

In the preferred construction, in order to attain access to interior holding zone or pouch 24 of container or housing 21, a notch or slit 25 is formed along one edge of container 21. In this regard, care must be exercised to prevent notch 25 from extending inwardly from the side edge so as to extend into holding zone or pouch 24. In this way, holding zone or pouch 24 is completely sealed from the ambient surrounding. However, any individual, wishing to open holding zone or pouch 24, is capable of doing so, whenever desired, by merely applying a tearing force to notch 25, causing notch 25 to extend into holding zone or pouch 24. In this way, zone 24 is maintained completely sealed from the ambient surroundings until access to zone 24 is sought by the user.

In the preferred embodiment, prior to sealing side walls or panels 22 or 23 to each other to form container or housing 21, super absorbent, cotton-based wicking means 30 is positioned within holding zone or pouch 24. In addition, the air freshening/deodorizing composition is also placed in holding zone or pouch 24, typically in fully absorbed, dispersed, cooperating interengagement with super absorbent cotton wicking means 30. However, if wicking means 30 is fully absorbed with the air freshening/deodorizing composition and excess composition remains, the excess composition merely pools within holding zone 24, remaining in direct contact with wicking means 30. Consequently, whenever container or housing 21 is open, as detailed above, and the air freshening/deodorizing composition is dispensed, wicking means 30 is maintained fully saturated by absorbing the excess air freshening/deodorizing composition until all of the excess formulation has been fully absorbed and all of the absorbed composition has been completely dispensed.

As is apparent from FIGS. 1 and 2, as well as the foregoing detailed disclosure, air freshening/deodorizing container and system 20 of the present invention may comprise any size or shape with interior, sealed holding zone 24 also comprising any desired size, shape or configuration. However, in order to employ the teaching of the present invention, cotton wicking means 30 must be mounted within holding zone 24 substantially filling the entire holding zone. In this way, complete absorption and distribution of all air freshening/deodorizing composition contained therein is assured.

Furthermore, wicking means 30 must also be positioned in holding zone 24 in an area which will be directly adjacent notch 25 or any other opening means incorporated with container 21. As is apparent from this disclosure, in order to attain the desired air freshening/deodorizing effect, with the composition absorbed within wicking means 30 being dispensed through the open zone, when formed, wicking means 30 must be positioned in cooperating association with the exit portal in order to assure that the desired dispensing of the air freshening/deodorizing composition to the surrounding ambient air is achieved.

In the preferred embodiment of the present invention, as discussed above, notch 25 is employed in order to open container 21 through the sealed zone thereof, to obtain access to holding zone 24 and wicking means 30. In this way, a safe, easy, and convenient opening of container and system 20 is attained. By employing notch 25, the user is capable of controlling the size of the opening being made, thereby enabling the user to form a portal through which the air freshening/deodorizing composition can exit which is directly dependant upon the amount of air freshening or deodorizing desired.

By virtually removing the entire top half of container or housing 21, maximum dispensing of the air freshener/ deodorizing composition is attained. However, if the user desires a slower rate of dispensing, only a portion of the top part of container 21 would be opened, so as to prevent excessive dispersion of the air freshening/deodorizing composition from wicking means 30 through the portal formed by the user.

In FIG. 4, an alternate controlled opening system is disclosed wherein a plurality of holes or portals 33, 34, 35 and 36 are formed in side wall 22 of container 21. Since holes 33, 34, 35 and 36 are formed through side wall 22, these holes provide dispensing portals for enabling the air freshening/deodorizing composition to exit from holding zone 24 to the ambient surrounding. In order to prevent unwanted, early dispersion of the air freshening/deodorizing composition, prior to the user's desire, an elongated sealing strip 38 is mounted in overlying sealing interengagement with portals 33, 34, 35 and 36. In this way, holding zone 24 is completely sealed from the ambient surroundings and the desired, long-term retention of air freshening/deodorizing composition within holding zone 24 is provided.

Whenever the user is ready to employ air freshening/deodorizing container and system 20, sealing strip 38 is employed by pulling sealing strip 38 away from one or more of the portals otherwise maintained closed by sealing strip 38. As depicted in FIG. 4, sealing strip 38 is removed from portals 35 and 36, while maintaining portals 33 and 34 completely sealed. In this way, an average rate of dispersion of the air freshening/deodorizing composition is attained.

As is apparent from the foregoing disclosure, by removing sealing strip 38 from the desired number of portals, the precisely desired rate of dispersion of the air freshening/deodorizing composition is realized. If maximum distribution is desired, sealing strip 38 is completely removed. However, any other rate of dispersion can be easily attained by uncovering the desired number of portals otherwise sealed by strip 38. In this way, the consumer maintains complete control over the rate of dispersion of the air freshening/deodorizing composition while also assuring that prior to use, the air freshening/deodorizing composition is securely retained in sealed interengagement within container 21, with the composition being incapable of being dispersed or permeated through side walls or panels 22 or 23.

In the preferred embodiment, the air freshening/deodorizing composition employed in system 20 of the present invention comprises the uniquely constructed formulation designed specifically for providing a concentrated, potent, long-lasting air freshening and/or deodorizing effect. In accordance with the present invention, the air freshening/deodorizing composition comprises between about 90% and 99% of one or more oil-based fragrances and between about 1% and 10% by weight of a fixative for the oil-based fragrance.

In the preferred embodiment, the fixative employed in the composition of the present invention comprises methyl hydrogenated rosinate. Methyl hydrogenated rosinate is the ester of methyl alcohol and the hydrogenated mixed long chain acids derived from rosin. It has been found that this particular composition works most effectively as a fixative in providing a superior air freshening/deodorizing composition, with the preferred amount being 5% by weight.

In addition to the methyl hydrogenated rosinate, the composition of the present invention incorporates, in the preferred embodiment, a plurality of oil-based fragrances to provide the desired air freshening and/or deodorizing effect. Although a wide variety of oil-based fragrances can be employed in carrying out the present invention, without departing from the scope of the present invention, it has been found that the preferred oil-based fragrances are selected from the group consisting of fruity notes, spices, cloves, eucalyptus, floral notes, jasmine, lavenders, wintergreen, spearmint, and wood notes. By employing one or a combination of these oil-based fragrances in the preferred quantity of 95% by weight of the entire composition, the desired air freshening and/or deodorizing fragrance is attained and the desired long-lasting, air freshening/deodorizing effect is realized.

In FIG. 3, the preferred embodiment of each of the side walls or panels 22 and 23 is depicted. Preferably, side walls or panels 22 and 23 comprise identical constructions, with both panels incorporating the identical integrally bonded multi-layered configuration. In FIG. 3, for exemplary purposes only, a portion of side wall panel 22 is shown in a greatly enlarged cross section in order to depict each of the plurality of integrally affixed layers forming side wall 22. As is apparent from the disclosure, panel 23 comprises an identical construction.

In the preferred embodiment, side wall or panel 22 and 23 comprises five separate and distinct independent layers, each of which are integrally bonded in secure, affixed interengagement to each other. The first or outer surface layer 41 comprises a polyester film, preferably having a thickness of about 48 gauge. Although other materials and thicknesses may be used for layer 41, polyester film is preferred in order to enable the surface of the layer to be printed upon.

The middle layer of side wall 22 is layer 43 which comprises a thin metal foil material. Preferably, metal foil layer 43 comprises a thickness ranging between 0.0001 and 0.0005 inches, with a thickness of 0.0003 inches being preferred.

In order to securely bond metal foil layer 43 to polyester film layer 41, layer 42 is employed. Preferably layer 42 comprises a low density polyethylene film having a thickness of about 0.00075 inches. Although other bonding films and other thicknesses may be employed, low density polyethylene is preferred and has proven to provide the desired intimate affixation of foil layer 43 to polyester layer 41.

The final two layers are layers 44 and 45. Layer 44 is similar in function to layer 42 and provides the desired secure bonding of foil layer 43 to layer 45. Although any suitable bonding film and thickness may be employed, layer 44 preferably comprises ethylene acrylic acid copolymer with a thickness of about 0.0015 inches.

Inside layer 45 of side wall 22 preferably comprises a film of linear low density polyethylene. Preferably, the thickness of layer 45 is about 0.00125 inches. The composition of layer 45 is particularly important, since the secure affixation of side wall 22 with side wall 23 is achieved by heat-sealing the outer peripheral edges of side walls 22 and 23 to each other.

In the preferred embodiment, side walls 22 and 23 are placed in overlying relationship with each other and, at the appropriate process time, the contacting surfaces of layer 45 of side walls 22 and 23 are intimately affixed together to form the desired, completely sealed container 20. By employing linear low density polyethylene film as layer 45, the desired complete sealed, bond affixation of side walls 22 and 23 is assured.

In FIG. 5, a further embodiment of the present invention is depicted. In this embodiment, as with the embodiments detailed above, air freshening/deodorizing system 20 comprises housing or container 21, which is formed from integrally bonded, multi-layered side walls or panels 22 and 23. In addition, this embodiment comprises wicking means 30 preferably formed from cotton material within which the desired air freshening/deodorizing composition is retained for distribution to the ambient surroundings.

In order to provide enhanced control over the rate of dispersion of the air freshening/deodorizing composition contained within wicking means 30, this embodiment of air freshening/deodorizing system 20 also incorporates a separate and independent permeable membrane layer 50 positioned between side wall 22 and wicking means 30. Preferably, permeable membrane layer 50 comprises an overall size and shape substantially equivalent to the size and shape employed for side walls or panels 22 and 23 and is securely affixed as part of system 20 by intimately bonding the outside peripheral edge of permeable membrane layer 50 between side walls or panels 22 and 23. In this way, the desired, completely sealed container 21 is easily attained with permeable membrane layer 50 controllably positioned between side wall 22 and wicking means 30.

As with the previous embodiments, whenever the dispensing of the air freshening/deodorizing composition is desired, dispensing system 20 is opened, using any desired access means incorporated into dispensing system 20. In particular, any of the access systems detailed above can be employed, with equivalent efficacy, with the embodiment of dispensing system 20 depicted in FIG. 5.

If desired, an alternate access system can be employed as shown in FIG. 5. In this access system, a flap member 51 is formed in side wall or panel 22 by incorporating a plurality of flap-defining notches 52 in the top surface of side wall or panel 22. In the preferred construction, flap-forming notches 52 extend from the outside surface of side wall or panel 22 to metal layer 43 of side wall or panel 22, in order to assure that the interior of dispensing system 20 is sealed and the air freshening/deodorizing composition is not dispensed prematurely.

Whenever a consumer is ready to employ dispensing system 20, flap 51 is held by suitable means, such as an access tab, which enables flap 51 to separate from side wall or panel 22, revealing permeable membrane 50. Once flap 51 has been opened to the desired extent, the air freshening/deodorizing composition contained in wicking means 30 is capable of passing through the pores of permeable membrane 50 and into the surrounding ambient air.

By constructing permeable membrane 50 in the manner consistent with the molecular structure of the air freshening/deodorizing composition being employed, the rate of dispersion of the air freshening/deodorizing composition into the ambient air is precisely controlled automatically. Furthermore, the use of permeable membrane 50 assures a continuous, dependable and completely repeatable rate of dispersion of the air freshening/deodorizing composition into the ambient surroundings.

As is evident from this disclosure, flap 51 may be constructed in any desired size and shape. As a result, if desired, flap 51 may be constructed with flap forming notches 52 formed in side wall or panel 22 in a manner which would substantially encompass a major portion of side wall or panel 22, as shown in FIG. 6. This enables virtually all of permeable membrane 50 to be exposed once flap 51 was opened. Although this would enable a greater quantity of the air freshening/deodorizing composition to be dispersed into the ambient surroundings, the rate of dispersion of the air freshening/deodorizing composition is still controlled by the pore size of permeable membrane 50. In this way, a continuous, substantially constant rate of dispersion is assured.

By specifically formulating permeable membrane layer 50 with a precisely desired pore size and employing particularly selected fragrances having desired molecular characteristics, the overall effectiveness and longevity of dispensing system 20 of the present invention is substantially enhanced and controlled. Furthermore, by employing permeable membrane layer 50 as part of dispensing system 20, substantially stronger concentrations of the air freshening/deodorizing composition may be employed without fear that the potency of the air freshener/deodorizer composition will be overpowering in its initial stages.

By controlling the rate of dispersion of the fragrance from the wicking means to the ambient surroundings, higher concentrated solutions of the air freshener/deodorizing composition can be employed and are efficiently and automatically dispensed, producing a continuous level of air freshening for the entire useful life of the air freshening/deodorizing composition. As a result, a highly effective and desirable dispensing system is realized.

In FIG. 6, a further alternate embodiment of the air freshening/deodorizing dispensing system 20 of the present invention is depicted. In this embodiment, dispensing system 20 incorporates a housing or container 21 formed from side walls of panels 22 and 23 in the manner detailed above. However, in order to provide a further enhanced construction, this embodiment employs permeable membrane layer 50 along with a second permeable membrane layer 55.

In the construction of this embodiment, membrane layers 50 and 55 comprise a size and shape substantially equivalent to or less than the size and shape of side walls or panels 22 and 23. If desired, membrane layers 50 and 55 are integrally affixed and secured between side walls or panels 22 and 23 as detailed above. In addition, if desired, permeable membrane layers 50 and 55 are intimately bonded to each other to form a separate and independent dispersion controlling member which comprises an internal retaining zone 56. Retaining zone 56 is employed to hold and securely retain wicking means 30. By forming a completely enclosed, independent dispersion controlling member within which wicking means 30 is securely retained, an easily assembled, dispensing system 20 is obtained which is easily employed to provide continuous dispersion of the fragrance at a fixed rate.

In accordance with the present invention, permeable membrane layers 50 and 55 may comprise any desired size and shape, provided the membrane layers are easily retained within housing or container 21 formed by side walls or panels 22 and 23. Clearly, regardless of the overall size of permeable membrane layers 50 and 55, the securement of wicking means 30 within permeable membrane layers 50 and 55 assures that all of the air freshening/deodorizing composition housed therein will be dispensed in a completely controlled manner, based upon the diffusion rate of the air freshening/deodorizing composition through the pores of permeable membrane layers 50 and 55.

In this embodiment, both side walls or panels 22 and 23 incorporate opening means formed therein to enable both sides of housing or container 21 to be opened. As depicted, enlarged flaps 51 are formed in both side walls or panels 22 and 23, to enable both side walls 22 and 23 to be opened, allowing access to both permeable membrane layers 50 and 55. As a result, greater surface area of the permeable membrane is exposed and a greater quantity of the air freshening/deodorizing composition is more readily dispensed into the ambient surroundings.

By employing this embodiment of the present invention, dispensing system 20 can be effectively employed in locations where forced air flow occurs, such as on air delivery registers or conduits. Using this embodiment, air is able to flow through dispensing system 20, continuously driving the dispersion of the desired air freshening/deodorizing composition through permeable membrane layers 50 and 55, carrying the fragrance in the air flow. As a result, the dispensing of the desired fragrance into the ambient surroundings is further enhanced and efficiently achieved.

Furthermore, in accordance with the present invention, any desired opening means can be employed in order to gain access to the permeable membrane. Although several alternate embodiments have been shown in the drawings, other constructions such as tear strips and integrally formed tear-filaments can be employed with equal efficacy. Consequently, all alternate constructions which achieve substantially the same results are encompassed within the scope of this invention.

In FIG. 7, a further alternate embodiment of the present invention is depicted. In this embodiment, dispensing system 20 incorporates a container or housing 21 formed from side walls or panels 22 and 23, as detailed above. In addition, two permeable membrane layers 50 and 55 are also employed in this embodiment.

As clearly depicted in FIG. 7, in this embodiment of the present invention, permeable membrane layers 50 and 55 are constructed with an overall size and shape substantially equivalent to the size and shape of side walls or panels 22 and 23, and are mounted in juxtaposed spaced relationship to each other with fragrance bearing means 58 sandwiched therebetween. When fully assembled, membrane layers 50 and 55 are integrally bonded to each other and to side walls or panels 22 and 23 about their respective outer peripheral edges, to form an integrally sealed container or housing 21 which defines dispensing system 20. In addition, any desired access means can be employed to enable the user to open dispensing system 20 and allow the fragrance retained therein to be dispensed through permeable membrane layers 50 and 55.

In addition, since two membrane layers are employed, with fragrance bearing means 58 positioned between permeable membrane layers 50 and 55, both side walls or panels 22 and 23 can both incorporate access means to enable either side or, if desired, sides of container or housing 21 to be opened for fragrance dispensing therethrough.

In this embodiment, as with the previous embodiments detailed above, any desired fragrance dispensing system can be employed. Although wicking means incorporating the desired fragrance composition, as fully detailed above, may be positioned between permeable membrane layers 50 and 55 of this embodiment, FIG. 7 depicts an alternate construction wherein a unitary fragrance holding or bearing member 58 is depicted.

As shown, fragrance bearing member 58 comprises a solid construction or a gel construction securely retained between permeable membrane layers 50 and 55. If desired, any type of fragrance bearing member may be employed in this embodiment or in any other embodiments detailed above. Regardless of the type of fragrance bearing member used, the dispersion of the desired fragrance through the side walls or panels 22 and 23 is attained.

By employing any of the embodiments shown in FIGS. 5–7, the membrane layer provides a controlled dispersion rate for the fragrance. In this way, assurance is provided that a continuous, precisely controlled level of fragrance is dispensed into the ambient surroundings, based upon the desired parameters sought by the manufacturer or the consumer.

Furthermore, permeable membrane layers 50 and 55 may be formed from any suitable material capable of providing a layer compatible with side walls or panels 22 and 23, as well as incorporating a pore size consistent with the molecular structure of the fragrance to be dispersed therethrough. Preferably, permeable membrane layers 50 and 55 are formed from polymeric plastic films or sheets which are impermeable to liquids but allow vapors to pass therethrough. Generally, any suitable polymeric film or sheet can be employed, such as sheets or films formed from polyurethane, polyethers, polyesters, polypropylenes, polystyrenes, and combinations thereof.

In FIGS. 8 and 9, a still further embodiment of the present invention is depicted. In this embodiment, as with the embodiments detailed above, air freshener/deodorizer system 20 comprises housing or container 21, which is formed from integrally bonded, multi-layered side wall or panels 22 and 23. However, as is fully detailed herein, this embodiment of the present invention incorporates odor absorbing material 70 contained within housing or container 21 in order to provide the desired air freshening or deodorizing of the ambient surroundings.

In order to attain the desired air freshening or deodorizing results, one or more odor absorbing material 70 are contained within housing or container 21. Preferably the odor absorbing material employed in the present invention comprises one or more selected from the group consisting of activated charcoal or active carbon, zeolites, baking soda, silica gel, silica molecular sieves, activated alumina, kieselguhr, fullers earth, and clay minerals. In accordance with the present invention, any of these compounds may be employed either independently or in combination, in order to provide the desired odor absorbing characteristics.

Although the desired odor absorbing material can be merely contained within housing 21 of the present invention, the preferred construction employs a microporous or permeable membrane, preferably formed in a pouch or holder configuration, within which the odor absorbing material 70 is retained. This preferred construction is depicted in FIGS. 8–9.

In the preferred embodiment, odor absorbing material 70 is retained within pouch or container 73 which is formed from microporous or permeable membranes 74 and 75. Although pouch/container 73 can be constructed in any desired size and shape, it is generally preferred that pouch/container 73 comprise overall dimensions smaller than container 21, in order to assure ease of insertion and retention of pouch/container 73 therein.

Microporous or permeable membrane 74 and 75 are preferably integrally attached to each other about their outer peripheral edges, in the manner detailed above in regard to the other embodiments, in order to form pouch/container 73 with an interior chamber 76. In this way, odor absorbing material 70 can be placed within chamber 76 for secure retention therein.

In this embodiment, microporous or permeable membrane layers 74 and 75 may be formed from any suitable material which is capable of retaining the desired odor absorbing material 70, while also allowing the ambient air to pass through the pores of the microporous or permeable membrane. In general, it has been found that microporous or permeable membrane layers 74 and 75 are preferably formed from one selected from the group consisting of woven or non-woven, synthetic or natural fibers integrally joined together, wood pulp, and plastic films or sheets.

The principal controlling factor regarding the material to be selected for microporous or permeable membrane layers 74 and 75 is the pore size of the microporous or permeable membrane layer. Since most odor absorbing materials 70 comprise small diameter powder-like or gel-like structure, the pore size of microporous or permeable membrane layers 74 and 75 must be formed to securely retain odor absorbing material 70, without allowing any portion of odor absorbing material 70 to pass through microporous or permeable membrane layer 74 and 75. However, except for this principal limitation, any desired material, construction, and configuration can be employed without departing from the scope of this invention.

In regard to the use of plastic or polymer-based films or sheets, suitable films or sheets may be formed from polyurethane, polyether, polyesters, polypropylenes, polystyrenes, and copolymer combinations thereof. Furthermore, suitable microporous or permeable membrane layers 74 and 75 can also be formed from acrylic copolymers, polymers or copolymers, such as combined with or formed on a non-woven nylon support. Although these materials have been found to provide effective microporous or permeable membrane layers which are formable into a pouch or container 73, any other type of suitable material can be employed with equal efficacy.

In addition to preventing unwanted transfer of odor absorbing material 70 through microporous or permeable membrane layers 74 and 75, microporous or permeable membrane layers 74 and 75 can also be selected to control the rate of transfer of the ambient air into odor absorbing material 70. By varying the pore size incorporated in microporous or permeable membrane layers 74 and 75, any desired transfer rate can be attained. In this way, any desired product longevity or odor removing capabilities can be realized.

As with the previous embodiments, whenever the use of odor absorbing material 70 is desired, system 20 is opened, using any desired access means incorporated into system 20. In particular, any of the access systems detailed above can be employed, with equivalent efficacy. The embodiment of system 20 depicted in FIG. 8 is provided as an example of one typical construction.

In the access system shown in FIG. 8, flap 51 is formed in side wall or panel 22 by incorporating a plurality of flap-defining notches 52 in the top surface of side wall or panel 22. In the preferred construction, flap-forming notches 52 extend from the outside surface of side wall or panel 22 to metal layer 43 of side wall or panel 22, in order to assure that the interior of system 20 is sealed and odor absorbing material 70 is not prematurely exposed to the ambient surroundings.

Whenever a consumer is ready to employ system 20, flap 51 is held by suitable means, such as an access tab, which enables flap 51 to separate from side wall or panel 22, revealing microporous or permeable membrane pouch or container 73. Once flap 51 has been opened to the desired extent, ambient air is capable of passing through the pores of microporous or permeable membrane layers 74 and 75, into odor absorbing material 70.

By constructing microporous or permeable membrane layers 74 and 75 in the manner consistent with the molecular structure of ambient air components, the rate of dispersion of the air into odor absorbing material 70 is precisely controlled. Furthermore, the use of microporous or permeable membrane layers 74 and 75 assures a continuous, dependable and completely repeatable rate of dispersion of the ambient air into odor absorbing material 70.

As is evident from this disclosure, flap 51 may be constructed in any desired size and shape. As a result, if desired, flap 51 may be constructed with flap forming notches 52 formed in side wall or panel 22 in a manner which would substantially encompass a major portion of side wall or panel 22, as shown in FIG. 8. This enables virtually all of microporous or permeable membrane layers 74 and 75 to be exposed once flap 51 was opened. Although this would allow a greater quantity of the ambient air to be exposed to odor absorbing material 70, the rate of transfer of the ambient air is still controlled by the pore size of microporous or permeable membrane layers 74 and 75. In this way, a continuous, substantially constant rate of transfer is assured.

In accordance with the present invention, microporous or permeable membrane layers 74 and 75 may comprise any desired size and shape, provided the membrane layers are easily retained within housing or container 21, as formed by side walls or panels 22 and 23. As depicted, membrane layers 74 and 75 comprise a size and shape smaller than the size and shape of side walls or panels 22 and 23, in order to provide ease of assembly. If desired, membrane layers 74 and 75 may be integrally affixed and secured between side walls or panels 22 and 23, as detailed above. Clearly, regardless of the overall size of microporous or permeable membrane layers 74 and 75, the secure retention of odor absorbing material 70 within microporous or permeable membrane layers 74 and 75 assures that all of the odor absorbing material housed therein will be employed in a completely controlled manner, based upon the transfer rate or diffusion rate of the ambient air through the pores of microporous or permeable membrane layers 74 and 75.

In the embodiment depicted in FIG. 8, both side walls or panels 22 and 23 incorporate opening means formed therein to enable both sides of housing or container 21 to be opened. As depicted, enlarged flaps 51 are formed in both side walls or panels 22 and 23, to enable both side walls 22 and 23 to be opened, allowing access to both microporous or permeable membrane layers 74 and 75. As a result, greater surface area of the permeable membrane is exposed and a greater quantity of the ambient air is able to easily pass through microporous or permeable membrane layers 74 and 75 for being exposed to odor absorbing material 70 contained therein.

By employing this embodiment of the present invention, system 20 can be effectively employed in any desired location where air circulation is present. In particular, one applicable location is found where forced air flow occurs, such as on air delivery registers or conduits. Using this embodiment, ambient air is able to flow through system 20, continuously exposing the ambient air to odor absorbing material 70 by passing through microporous or permeable membrane layers 74 and 75. In this way, unwanted odors are removed from the ambient air and the ambient surroundings are enhanced.

Furthermore, in accordance with the present invention, any desired opening means can be employed in order to gain access to microporous or permeable membrane layers 74 and 75. Although several alternate embodiments have been shown in the drawings, other constructions such as tear strips and integrally formed tear-filaments can be employed with equal efficacy. Consequently, all alternate constructions which achieve substantially the same results are encompassed within the scope of this invention.

As detailed above, in the embodiment shown in FIGS. 8 and 9, two membrane layers are employed, with odor absorbing material 70 positioned between microporous or permeable membrane layers 74 and 75. As a result, both side walls or panels 22 and 23 can incorporate access means to enable either side or, if desired, both sides of container or housing 21 to be opened for maximizing the exposure of the odor absorbing material to the ambient air. However, if desired, a single membrane layer can be employed, as shown in FIG. 5, with the odor absorbing material retained between the membrane layer and one side of container or housing 21. In this embodiment, only the panel of container or housing 21 which is adjacent to the microporous or permeable membrane would incorporate the flap or opening means.

In FIGS. 10–14, still further alternate embodiments of the present invention are detailed. By referring to these drawings, along with the following detailed disclosure, the construction of these further alternate embodiments can best be understood. In particular, these embodiments comprise unique combinations of the embodiments detailed above as well as the combinations of these elements with alternate compounds included therein.

By employing the present invention, an air freshening and/or deodorizing system is attained which provides a pleasing fragrance to be dispersed throughout a desired area while also simultaneously providing odor absorption capabilities for removing offensive odors from the desired area. In this way, the dual cooperative efforts of both compositions detailed above are simultaneously provided.

Figure 10:
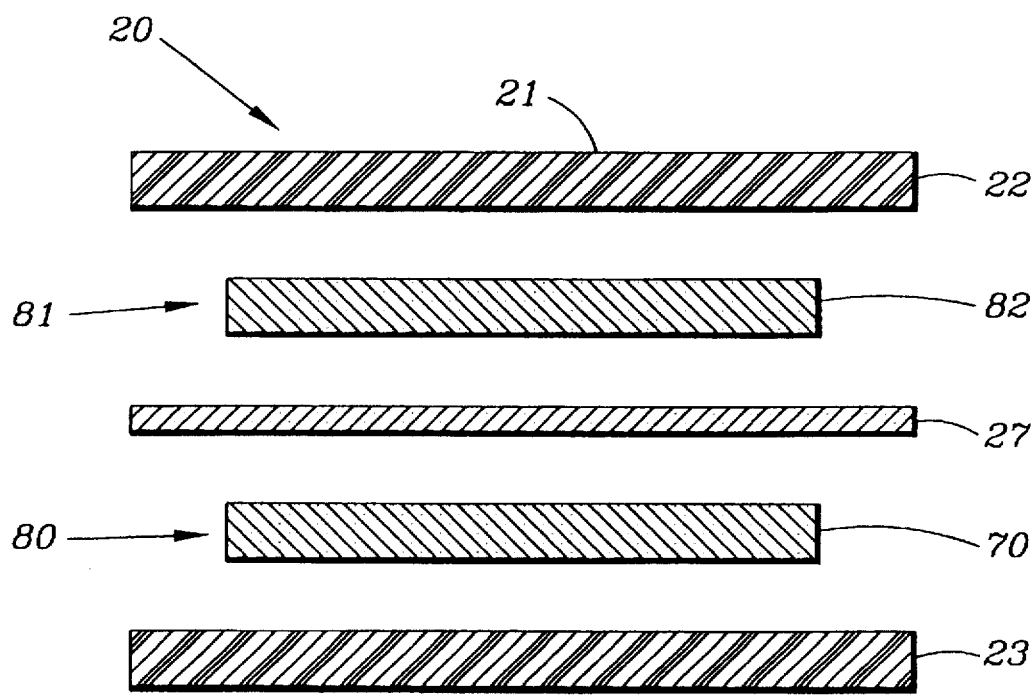

In FIG. 10, one construction of these additional alternate embodiments of air freshening/deodorizing system 20 is depicted. In this embodiment, air freshening/deodorizing system 20 is constructed in a manner generally similar to the embodiments detailed above. However, in this embodiment, air freshening/deodorizing system 20 comprises a container 21 for the air freshening composition and the odor absorbing composition, with the container preferably formed from three multi-layered panels 22, 23, and 27. In the preferred construction, panels 22, 23, and 27 are all integrally sealed with each other, about their outer peripheral edges, as fully detailed above in the previous embodiments. By integrally sealing panels 22, 23, and 27 about their entire outer peripheral surfaces, an interior holding zone or pouch 80 is formed between panels 22 and 27, while a similar interior holding zone or pouch 81 is formed between panels 27 and 23.

In order to complete the construction of this embodiment of air freshen system 20, fragrance producing means 82 is positioned within interior holding zone 80, prior to its closure and sealing, and odor absorbing means 70 is positioned within interior holding zone 81 prior to the sealing of holding zone 81. In this way, odor absorbing/deodorizing system 20 comprises separate and independent sealed holding zones 80 and 81, each of which incorporate a separate, independent, and completely isolated means for producing a desirable fragrance as well as means for removing offensive odors from a desired area.

As a result, by opening air freshening/deodorizing system 20, using the various alternate constructions detailed above, both fragrance producing means and odor absorbing means can be simultaneously accessed for providing independent results simultaneously or, if desired, constructed for separate and independent use. If desired, an individual using this embodiment of air freshening/deodorizing system 20 is able to provide the desired fragrance to the air, whenever desired, without exposing the odor absorbing means to the ambient air. Similarly, if odor absorbing is desired, interior holding zone 81 would be accessed to enable the offensive odors in the area to be absorbed by odor absorbing means 70, without releasing the fragrance retained by fragrance producing means 80, which remains sealed in interior holding zone 80.

Figure 11:
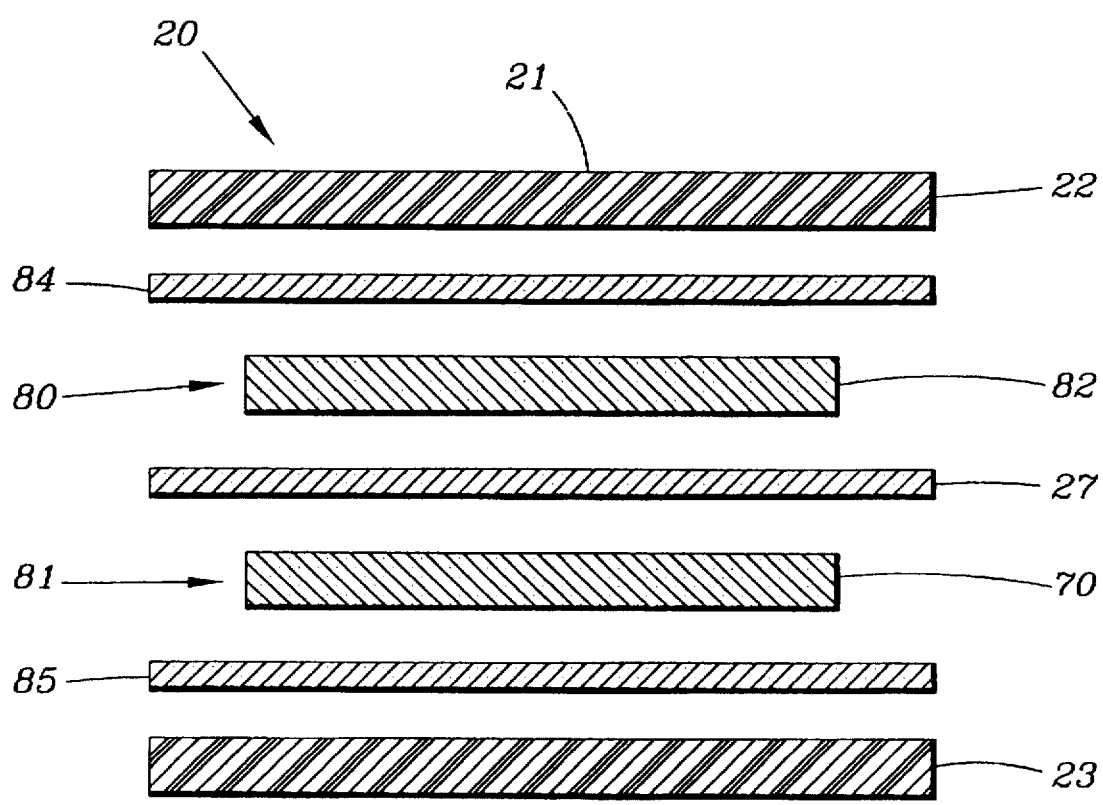

In FIG. 11, a further alternate embodiment of air freshening/deodorizing system 20 is depicted, which is similar to the embodiment depicted in FIG. 10. In this alternate embodiment, container or housing 21 is constructed in the same manner detailed above in reference to FIG. 10, with container 21 comprising panels 22, 23, and 27 each of which are integrally sealed to each other to form interior holding zones 80 and 81. In addition, this embodiment also incorporates fragrance producing means 82 positioned within interior holding zone 80 and odor absorbing means 70 positioned within interior holding zone 81.

In order to provide controlled release of the fragrance from fragrance producing means 82 as well as controlled absorption of the offensive odors from the ambient conditions, this embodiment of air freshening/deodorizing system 20 also incorporates a permeable membrane layer 84 positioned between panel 22 and fragrance producing means 82 to provide the desired control over the release of the fragrance into the ambient air once panel 22 has been opened. Similarly, in the preferred construction of this embodiment, a permeable membrane layer 85 is positioned between panel 23 and odor absorbing means 70 to control the rate of absorption of the offensive odors from the ambient air once interior holding zone 81 has been opened.

As detailed above in reference to FIGS. 8 and 9, odor absorbing means 70 of the present invention comprises at least one selected from the group consisting of activated charcoal or activated carbon, zeolites, baking soda, silica gel, silica molecular sieves, activated alumina, kieselguhr, fullers earth, and clay minerals. In accordance with the present invention, any of these compounds may be employed either independently or in combination in order to provide the desired odor absorbing characteristics.

In addition, depending upon the physical size of the compounds employed as odor absorbing means 70, in combination with the size of the apertures formed in housing or container 21 for enabling odor absorbing means 70 to be exposed to the ambient air, the necessity or desirability of employing the construction shown in FIG. 10 or the construction shown in FIG. 11 becomes evident. Clearly, if the size of the compound forming the odor absorbing means 70 is incapable of passing through the apertures formed in container 21, the construction shown in FIG. 10 can be employed without requiring the use of a membrane layer. However, if smaller sized crystals or compounds are employed as the desired odor absorbing means 70, the construction depicted in FIG. 11 would be preferred, with permeable membrane layer 85 present to prevent any unwanted dispersion or release of odor absorbing means 70 from container 21.

Figure 12:
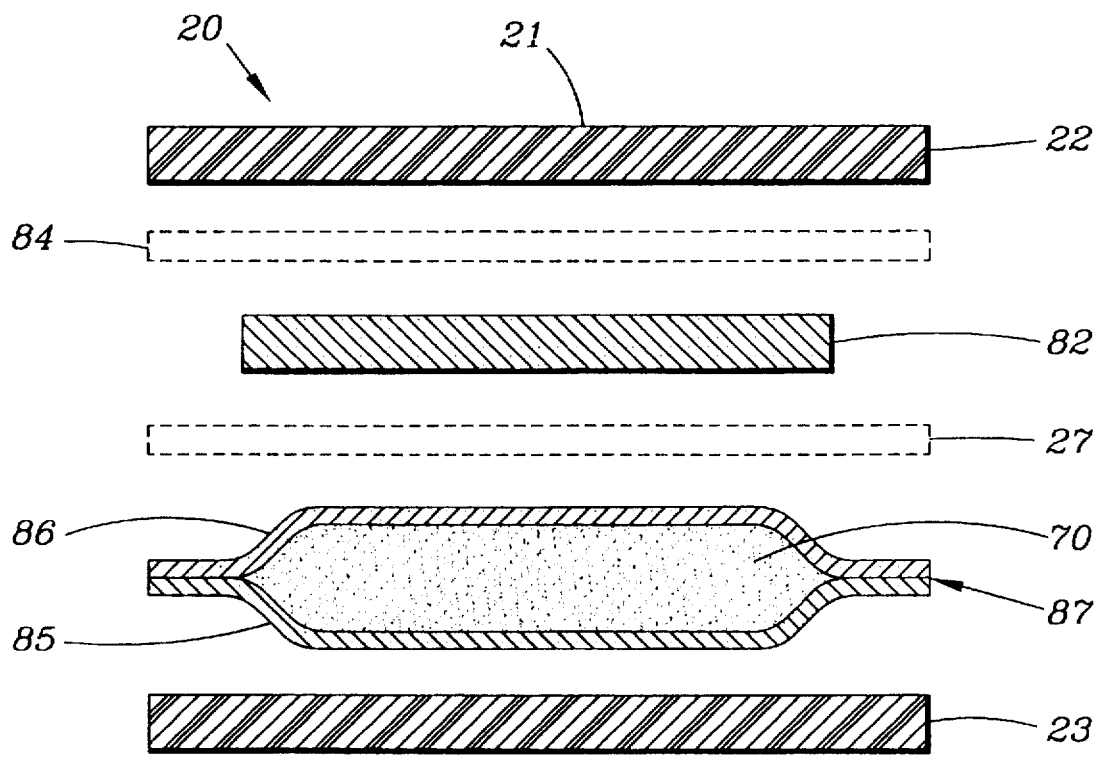

As detailed above in reference to FIGS. 8 and 9, odor absorbing means 70 is preferably retained within a separate, independent, integrally sealed pouch or container 87, formed from microporous or permeable membrane layers 85 and 86, as depicted in FIG. 12. In this embodiment, pouch/container 87 can be constructed in any desired size and shape. However, it is preferred that pouch/container 87 is constructed with dimensions smaller than container 21 in order to assure ease of insertion and retention of pouch/container 87 within container 21.

In addition, in this embodiment, container 21 also incorporates odor/producing means 82 cooperatively associated therewith, in order to provide the desired fragrance simultaneously with the ability to absorb odors from the ambient surroundings. If desired, as depicted in FIG. 12, fragrance producing means 82 may incorporate microporous or permeable membrane layer 84, preferably positioned between panel 22 and fragrance producing means 82. Since the inclusion of microporous or permeable membrane layer 84 is optional, membrane layer 84 is depicted in FIG. 12 in phantom.

A further component that may be incorporated into the embodiment of FIG. 12 is panel 27, also shown in phantom in FIG. 12. If two, separate, independent interior holding zones 80 and 81 are desired, panel 27 is positioned between panels 22 and 23 as detailed above in reference to FIGS. 10 and 11. However, if the independent isolation of fragrance producing means 82 from odor absorbing means 70 is not required, panel 27 may be eliminated.

With this embodiment, it has been found that panel 27 is not required, since odor absorbing means 70 is securely retained within pouch 87. As a result, microporous or permeable membrane 86 provides an effective barrier between odor absorbing means 70 and fragrance producing means 82, thereby enabling panel 27 to be eliminated, if desired.

In order to provide an effective combined air freshening/ deodorizing system 20, as depicted and discussed in reference to FIGS. 10–12, it is important that fragrance producing means 82 employed in combination with odor absorbing means 70 is constructed from fragrances which are not fully absorbed by odor absorbing means 70. In this regard, it has been found that fragrances formed from natural botanical ingredients are not absorbed by odor absorbing means 70 and provide a continuous production of fragrance, while offensive odors are absorbed by odor absorbing means 70.

Although any desired botanical fragrance can be employed, the preferred botanicals employed in the present invention comprise one or more fragrances selected from the group consisting of eucalyptus, floral notes, jasmine, lavender, wintergreen, spearmint, wood notes, wormwood, echinacea, lemongrass, calendula, balsam, oleoresins, tea tree, ginseng, licorice, and menthol. Although the foregoing botanicals are preferred, any other fragrance having similar characteristics, configurations, or structures can be employed with equal efficacy.

Typically, the preferred botanical fragrances are manufactured as oils, liquid extracts, or solids which may be pulverized into any desired micron size. Consequently, these botanical fragrances can be employed in the present invention in any of the desired physical forms, without departing from the scope of the present invention.

In this regard, fragrance producing means 82 may comprise any of the desired botanical fragrances, in liquid form, used in combination with wicking means as fully detailed above in reference to FIGS. 1–7. In this regard, the desired botanical fragrance can be employed in its pure liquid form in conjunction with wicking means, can be employed in its solid form, or formed as a gel positioned within container 21, as detailed above in FIGS. 10–12.

In addition, if desired, fragrance producing means 82 may be constructed by employing an inert carrier within which the liquid fragrance is retained. In this regard, any desired inert carrier can be employed which is capable of absorbing the fragrances in their liquid form, retaining the fragrances therein, and slowly releasing the volatile fragrance to the ambient surroundings whenever container 21 has been opened. In addition, by employing inert carriers of this general configuration, crystal sizes can be selected to assure that the fragrance bearing crystal carriers are retained within container 21 by controlling the apertures formed in container 21 or employing membrane layer 84, as depicted in FIGS. 11 and 12.

Although any desired inert carrier can be employed for this purpose, it has been found that inert carriers formed from sodium chloride and cellulosic materials insoluble in the liquid oils or extracts formed by the preferred botanical fragrances are most effective. One product which has been found which is capable as functioning as an inert carrier in which the desired fragrances are retained for subsequent dispersion are Cargille absorbing fragrance carriers manufactured and distributed by Cargille Corporation of Cedar Knolls, N.J.

As is evident from the foregoing detailed disclosure, by employing either wicking means or inert carriers formed as solid crystals, the desired botanical fragrances can be imparted into any desired configuration, size, and form for providing fragrance producing means 82, as detailed above in reference to FIGS. 10–12. In addition, by assuring that botanical fragrances are employed, fragrance absorption by the odor absorbing means 70 is prevented and the dual purpose, combined air freshening/deodorizing system 20 of this embodiment of the present invention is realized.

If desired, the inert carrier materials detailed above can be formed as single tablets having a desired size and shape for being easily positioned within container 21. As a result, this embodiment of the present invention can be manufactured with the desired fragrances incorporated in the tablet, providing the desired fragrance producing means in an easily assembled effective construction.

Alternatively, crystals of the inert carrying material can be employed with the desired fragrance absorbed therein with the crystals placed within container 21 to provide the fragrance producing means 82 for these embodiments of the present invention. Depending upon the crystal's size, membrane layer 84 can be employed as discussed above, for controlling the rate of dispersion of the fragrance into the ambient air, as well as controlling unwanted dispersement of the fragrance crystals through the openings of container 21.

In those embodiments when fragrance producing means 82 is formed from crystals, the preferred construction employs microporous or permeable membrane 84 having pore sizes formed therein which are consistent and cooperative with the size of the crystals forming fragrance producing means 82. In this way, controlled dispersion of the fragrance is attained, while any unwanted dispersion of the crystals themselves is prevented. However, as discussed above, membrane layer 84 is not required, since the apertures formed in panel 22 of container 21 can also be sized in a manner which will assure the retention of any fragrance bearing crystals forming fragrance producing means 82.

Figure 13:
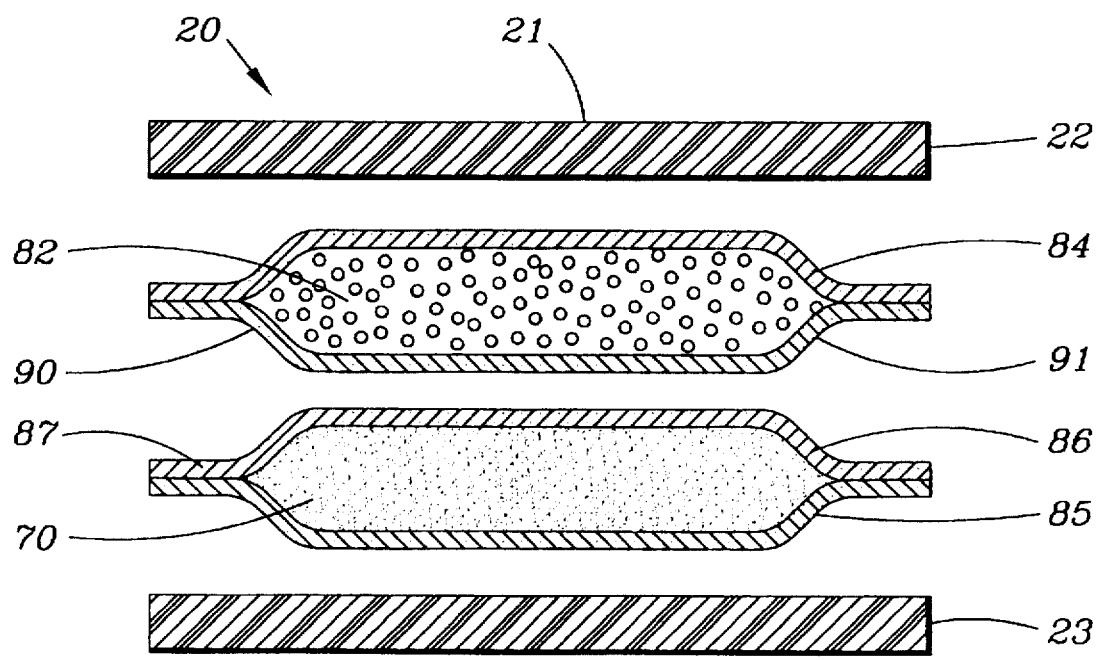

In FIG. 13, a further alternate embodiment of the present invention is depicted for providing combined air freshening and deodorizing system 20. In this embodiment, odor absorbing means 70, as detailed above in reference to FIG. 12, is retained within pouch 87, formed from microporous or permeable membrane layers 85 and 86. In the preferred construction, microporous or permeable membrane layers 85 and 86 are sealed about their outer peripheral surfaces in order to securely retain odor absorbing means 70 is a completely sealed configuration. In this way, complete control over the absorption of the ambient air is attained by selecting the desired porosity of membranes 85 and 86.

In the embodiment depicted in FIG. 13, fragrance producing means 82 is also securely mounted in a separate, independent, preferably sealed pouch or container 90 formed from microporous or permeable membrane layers 84 and 91. As detailed above in reference to pouch 87, pouch 90 is also preferably sealed about its outer peripheral surface by securely bonding or affixing membrane layers 84 and 91 to each other to securely retain odor producing means 82 therein.

Although any desired odor producing means or materials can be employed, including the wicking material and gel material detailed above, it has been found that the use of odor absorbing crystals is preferably employed within pouch 90. By providing a sealed pouch construction, unwanted release of the fragrance bearing crystals into the ambient air is prevented and the controlled release of the fragrance from the inert crystals is assured by having the crystals surrounded and sealed within microporous or permeable membrane layers 84 and 91.

Air freshening/deodorizing system 20 is completed by peripherally surrounding pouch 87 and pouch 90 within container or housing 21 which is preferably formed from panels 22 and 23. By employing this embodiment, complete control over the rate of dispersion of the fragrance and the rate of absorption by odor absorbing means 70 is provided, with each of the two active ingredients being maintained completely independent of each other. In addition, depending upon the membrane employed, the rate of dispersion of the fragrance and the rate of absorption by the odor absorbing means are completely separate and independent, controlled entirely by the particular microporous or permeable membrane layers selected for each component.

Furthermore, although container 21 is preferably formed from panels 22 and 23, with panels 22 and 23 being sealed to each other about their outer peripheral edges as detailed above, this embodiment of the air freshening/deodorizing system 20, as well as the embodiments detailed above in reference to FIGS. 10–12 may be retained in any desired container, without limiting the container construction to a multi-layer panel structure as detailed herein as the preferred structure. By employing two completely sealed and independent pouches 87 and 90, any alternate container construction can be employed without departing from the scope of this invention.

Figure 14:
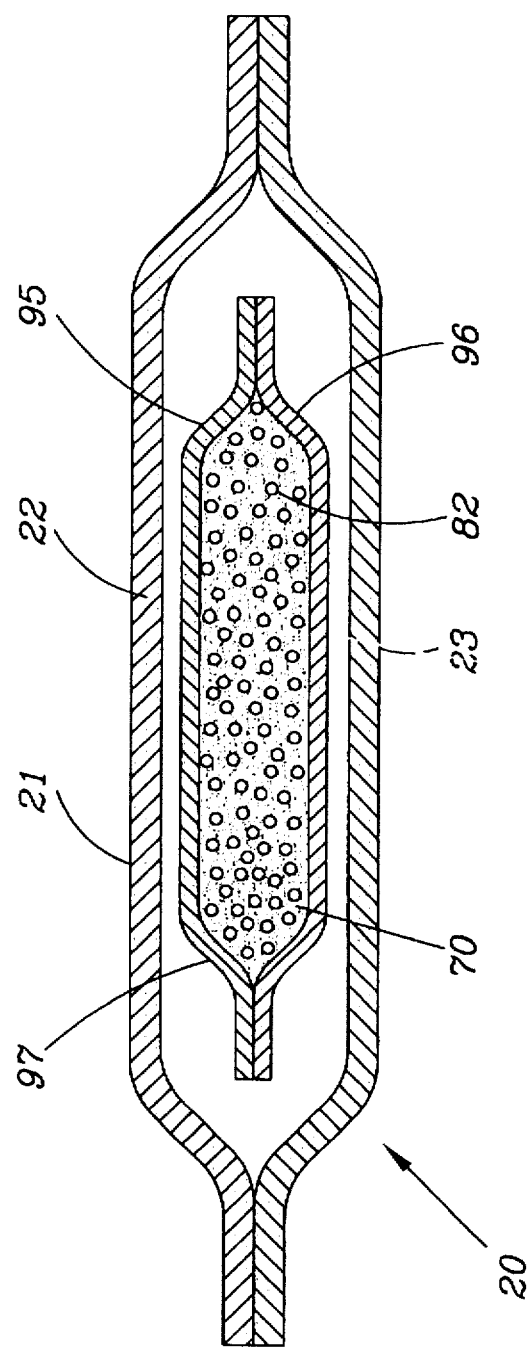

In FIG. 14 a further alternate embodiment of the present invention is depicted. In this embodiment, air freshening/deodorizing system 20 comprises a container 21 preferably formed from panels 22 and 23 which are sealed to each other about their outer peripheral mating edges, as detailed above. In this embodiment, odor absorbing means 70 and fragrance producing means 82 are intermixed with each other in a single assembly, retained by microporous or permeable membranes 95 and 96 which are formed into a sealed pouch 97. As discussed above, pouch 97 is formed by sealing the outer peripheral edges of microporous or permeable membranes 95 and 96 with the desired odor absorbing means 70 and fragrance producing means 82 retained therein.

In this embodiment, fragrance producing means 82 comprises solid materials within which a desired fragrance is absorbed. Since the fragrance retained by the solids is constructed using botanical fragrances, which are unaffected by odor absorbing means 70, these two components are capable of being intermixed in a single pouch 97 for providing their separate and independent functions, without interfering with each other.

In this embodiment, microporous or permeable membranes 95 and 96 are selected with a particular pore size which enables both fragrance producing means 82 and odor absorbing means 70 to function in their optimum manner without adversely affecting each other. In addition, although this embodiment of air freshening/deodorizing system 20 is depicted with container 21 formed from multi layer panels 22 and 23, it is evident to one of ordinary skill in the art that sealed pouch 97 can be retained in any desired container without departing from the scope of this invention.

As detailed above, the microporous or permeable membranes employed in the present invention may be formed from a wide variety of different materials and may comprise a wide variety of different constructions. In general, the microporous or permeable membrane coming within the scope of the present invention may comprise any desired material which incorporates a pore size consistent with the molecular structure of the fragrance to be dispersed therethrough and/or the odors to be absorbed by the odor absorbing material retained thereby. In addition, the microporous or permeable membrane must be consistent with the fragrance producing means and/or the odor absorbing means being retained thereby.

In general, it has been found that the microporous or permeable membrane is preferably formed from one or more materials selected from the group consisting of woven or non-woven, synthetic or natural fibers, integrally joined together, wood pulp, and plastic films or sheets. In addition, in regard to the use of plastic films or sheets, any suitable polymeric film or sheet can be employed such as sheets or films formed from polyurethane, polyethers, polyesters, polypropylenes, polystyrenes, acrylic copolymers, polymers or copolymers combined with or formed on a non-woven nylon support, and combinations thereof.

In most instances, the microporous or permeable membrane is constructed to be impermeable to liquids, while allowing vapors to pass therethrough. By controlling the pore size of the particular microporous or permeable membrane, precise control over the dispersion of the fragrance is attained when the fragrance producing means is incorporated therein. Similarly, the pores of the microporous or permeable membrane controls the air flow rate from the ambient air through the permeable membrane to the odor absorbing material, whenever the permeable membrane is employed for covering or peripherally surrounding the odor absorbing means. Regardless of which product is employed in combination with the microporous or permeable membrane, the same material may be employed or, if desired, different material for each of the components.

One product that has proven to be successful for containing odor absorbing means 70, as detailed above, is the use of a two-phase, lightweight, heat-sealable tissue material comprising a blend of thermoplastic fibers, manila hemp and other cellulose fibers. By employing microporous or permeable membranes comprised of a blend of thermoplastic fibers, manila hemp and other cellulose fibers, complete heat sealing of the odor absorbing material with adjacent membrane layers is easily achieved and a strong, easily handled, efficient and long-lasting permeable membrane container system is realized for odor absorbing means 70 and/or fragrance producing means 82.

Although numerous products can be employed as a microporous or permeable membrane, in accordance with the present invention, it has been found that microporous or permeable membrane products manufactured by Dexter Corporation of Windsor Locks, Conn., and sold as a specialty product bearing grade 11189, 11521, and 11212, provide desirable results. However, these products are included only as examples and other comparable products can be employed without departing from the scope of this invention.

As discussed above, a sealed, integral, holding pouch for either the odor absorbing material or the fragrance producing material is achieved in a wide variety of alternate ways. Typically, the materials are integrally bonded to each other, using suitable fastening means such as adhesives, glues, etc. Alternatively, the materials are fused to each other by heat sealing the outer peripheral edges thereof. Regardless of the method employed for effectively sealing microporous or permeable layers together to form an integral sealed pouch, the overall results detailed above are attained and a compact, easily handled product retaining pouch is realized.

In optimizing the efficacy of the odor absorbing material, it is preferable to maximize the surface area of the odor absorbing material so as to provide maximum area for absorption of the odors from the ambient air. As a result, it is most desirable to employ small particles or crystals of the odor absorbing material in order to attain maximum surface area.

In producing a viable product which optimizes the surface area of the odor absorbing material, while also providing a product which is commercially saleable, it has been found that extremely small particle sizes produce a powdering effect, which can escape through the pores of the permeable membrane into the ambient surroundings. As a result, a reasonable limitation must be placed on the particle size of the odor absorbing material in order to prevent unwanted powdering or product dispersion of the odor absorbing material into the ambient surroundings.

In this regard, some of the powdering can be controlled by using microporous or permeable membranes having small pores. However, by reducing the porosity of the microporous or permeable membrane, the air flow capability through the membrane is also reduced. Consequently, both factors must be controlled in a reasonable manner, in order to provide the odor absorbing characteristics being sought, both efficiently and usefully.

In the present invention, it has been found that by controlling the particle size of the odor absorbing material to range between about 2.5 microns and 500 microns, optimum results are attained. By employing odor absorbing material having a micron size falling within this range, it has been found that virtually no powdering is realized, while efficient, long-lasting, odor absorption results are attained. Furthermore, it has been found that the use of the odor absorbing material of these physical characteristics in combination with the microporous or permeable membranes detailed above provide the optimum results.

As is evident from the foregoing detailed disclosure, air freshening/deodorizing system 20 of the present invention can be implemented in a wide variety of alternate embodiments, without departing from the scope of this invention. However, regardless of which embodiment of the present invention is employed, a highly effective fragrance producing and/or deodorizing system is realized in a small, compact, easily used container. Furthermore, by employing the preferred construction wherein the container is formed from multi-layered panels, longterm storage and retention of the air freshening and/or deodorizing systems of the present invention are realized with no degradation of the systems being caused from such storage.

Instead, whenever required, the container is opened and the fragrance producing means and/or the odor absorbing means are immediately activated, ready to provide the desired functions for which they were retained. As a result, it is immediately apparent that all of the objects detailed above, are attained, along with the variety of uses to which the air freshening and/or deodorizing system 20 of the present invention can be employed.

It has been found, in addition to the numerous constructions and embodiments detailed above, the air freshening and/or deodorizing system of the present invention is also highly effective in being employed in clothes dryers, refrigerators, and other similar locations. By employing the air freshening and/or deodorizing system of the invention in these areas, the desired fragrance production and/or odor absorption is attained in a manner wherein air flow is promoted, thereby further enhancing the efficacy of the present invention.

It has also been found that the present invention is capable of satisfying a long-felt need for which no solution has been realized before the present invention. This need is with the control of odors caused by menstrual cycles, as well as by individuals who are incontinent. By incorporating the air freshening/deodorizing system of the present invention, preferably implemented in its odor absorbing form, absorption of undesirable odors is attained and virtually complete odor absorption is realized for problems that previously have been completely incapable satisfactory resolution. As result, by employing the present invention, a highly desirable result is attained in an area where no solution previously existed.

Although the construction detailed above for air freshening and/or deodorizing system 20 of the present invention are preferred, it has also been found that the fragrance producing means and the odor absorbing materials detailed above can be employed in an alternate construction to provide a unique, heretofore unattainable result. In this regard, it has been found that air freshening and deodorizing of an ambient area can be attained by employing the fragrance producing means and odor absorbing means in an aerosol delivery system (see FIG. 15). In this regard, by combining the solids detailed above within which the desired fragrance is retained and intermixing fragrance producing solids in combination with odor absorbing means, an aerosol delivery system is realized which simultaneously provides a desired fragrance to any particular area, while also dispersing odor absorbing means simultaneously therewith.

In Table I, the preferred formulation for a highly effective, air freshening and deodorizing composition capable of being dispensed in an aerosol delivery system is detailed, with each ingredient being defined with their preferred ranges. In addition, in Table II the preferred formulation is defined for each ingredient. Finally, in Table III, the composition of the aerosol delivery system is separately detailed.

TABLE I

| Ingredient | %/Weight |
|---|---|
| SDA 40-B (200 proof) | 65–90 |
| Odor Absorbing Material | 1–5 |
| Talc, USP #103 | 3–20 |
| Stearalkonium Hectorite | 1–5 |
| Propylene Glycol | 1–6 |
| Sorbitan Sequioleate | .1–3 |
| Fragrance Producing Means | 1–10 |

TABLE II

| Ingredient | %/Weight |
|---|---|
| SDA 40-B (200 proof) | 78.0 |
| Odor Absorbing Material | 2.0 |
| Talc, USP #103 | 10.0 |
| Stearalkonium Hectorite | 2.0 |

TABLE II-continued

| Ingredient | %/Weight |
| --- | --- |
| Propylene Glycol | 3.0 |
| Sorbitan Sequioleate | 1.0 |
| Fragrance Producing Means | 4.0 |

TABLE III

| Aerosol Fill | %/Weight | Grms/Can |
| --- | --- | --- |
| Air Freshening/Deodorizing Composition | 30.0 | 35.2 ± 1.0 |
| Isobutane Propellant | 70.0 | 81.8 ± 2.0 |

In order to produce the formulation for the air freshening/deodorizing composition for being dispensed in an aerosol delivery system, it is preferred to start with the SD alcohol 40B in a suitable container followed by the addition of the sorbitan sequioleate. Then, with mixing continuing throughout, the propylene glycol, the stearalkonium hectorite, talc, and the odor absorbing material are added. Once these ingredients are all thoroughly mixed, the desired fragrance bearing means are added. Once all ingredients are thoroughly mixed, the composition is added to the aerosol container, which is closed and sealed in the normal manner, thereby producing an aerosol delivery system ready for use.

As detailed above, the fragrance incorporated in the fragrance absorbing materials preferably comprises fragrances derived from botanicals, all of which are detailed above, in order to provide fragrances which are not absorbed by the odor absorbing material, and are able to function independently thereof. In addition, any of the odor absorbing materials detailed above can be employed in order to achieve the desired air freshening formulation for delivery in an aerosol system.

In this formulation, it has been found that the odor absorbing material preferably comprises Abscents deodorizing powders manufactured and sold by UOP Molecular Sieves of Mount Laurel, N.J. However, although the Abscents deodorizing powder has been found to be most effective in this delivery system, other odor absorbing materials can be employed with equal efficacy, without departing from the scope of this invention.

It has also been found that the fragrance producing materials and the odor absorbing materials can be employed in an aerosol delivery system providing an antifungal foot powder. As defined in Table IV, the preferred formulation for an antifungal foot powder in accordance with the present invention is detailed, with each ingredient defined with its preferred range, while Table V defines the same components with the preferred quantity of each composition detailed therein. Finally, Table VI details the components forming the aerosol delivery system.

TABLE IV

| Ingredient | %/Weight |
| --- | --- |
| SDA 40-B (200 proof) | 45-70 |
| Taluaftate, USP | 0.1-1.0 |
| Talc, USP #123 | 20-60 |
| Odor Absorbing Material | 1-5 |
| Tenoa WL-660 | 0.5-3 |
| Tenox BHT USP | 0.05-1 |
| Fragrance Producing Means | 0.1-5 |

TABLE V

| Ingredient | %/Weight |
| --- | --- |
| SDA 40-B (200 proof) | 56.0 |
| Taluaftate, USP | 0.44 |
| Talc, USP #123 | 39.46 |
| Odor Absorbing Material | 2.00 |
| Tenoa WL-660 | 1.50 |
| Tenox BHT USP | 0.10 |
| Fragrance Producing Means | 0.50 |

TABLE VI

| Aerosol Fill | %/Weight | Grms/Can |
| --- | --- | --- |
| Antifungal Foot Power Composition | 25.00 | 26.00 ± 1.5 |
| Isobutane Prop. | 75.00 | 78.00 ± 2.5 |

In order to intermix the components forming the antifungal foot powder, it is preferred that a clean, sanitized batch tank and mixer be employed and the SD alcohol 40B is added with moderate mixing. Then, the Tenox BHT is added followed by the addition of Tenoa WL-660.

Thereafter, the talc is added followed by the odor absorbing material. Once all of these ingredients are thoroughly mixed, with the odor absorbing material being well dispersed throughout the entire batch, the taluaftate is added followed by the addition of the fragrance producing means. Once all of the ingredients have been thoroughly mixed, with the mixing continuing throughout the entire process, the thoroughly mixed composition is added to an aerosol container for being sealed in the conventional manner. In addition, although any desired fragrance can be employed, in accordance with this invention, menthol is preferred.

In addition to the aerosol spray formulation detailed above, the odor absorbing material and fragrance producing means of the present invention can also be incorporated in other aerosol spray delivery systems. In this regard, the present invention can be implemented with cleaning spray formulations to enhance and improve the results attained from such cleaning spray systems. In addition, numerous other spray formulations can be enhanced and substantially improved by formulating the spray with the odor absorbing material and the fragrance producing means defined herein. As a result, all of the additional formulations and uses are considered to be within the scope of the present invention.

It will thus be seen that the objects set forth above, among those made apparent from the preceding description, are efficiently attained and, since certain changes may be made in the above constructions without departing from the scope of the present invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described my invention, what I claim as new and desire to secure by Letters Patent is:

1. A combined air freshening and deodorizing system for providing controlled, long-term release of an air freshening fragrance and absorption of odors from the ambient air, said system comprising A. a container incorporating a sealed holding zone;
   B. odor absorbing material contained within the holding zone and comprising one or more selected from the group consisting of activated charcoal or active carbon, zeolites, baking soda, silica gel, silica molecular sieves, activated alumina, kieselguhr, fullers earth, and clay minerals;
   C. fragrance producing means comprising
      a. a highly concentrated, long-lasting, air freshening fragrance comprising a formulation selected from the group consisting of compositions which are unable to be absorbed by the odor absorbing material, and
      b. an inert carrier for holding the fragrance composition and providing controlled release of the fragrance; and
   D. a portal zone
      a. formed in the container in a normally sealed configuration to prevent the release of the fragrance or the odor absorbing material from the holding zone, and
      b. controllably openable to enable the fragrance to be dispersed throughout the ambient air and to allow the air to contact the odor absorbing material while preventing the odor absorbing material or the fragrance bearing carrier from exiting from the holding zone into the ambient surroundings.

2. The air freshening and deodorizing system defined in claim 1, wherein said system further comprises
   E. holding means constructed for retaining the odor absorbing material and being mounted in the holding zone of the container.

3. The air freshening and deodorizing system defined in claim 2, wherein said holding means is further defined as being positioned in the holding zone in cooperative association with the portal zone for assuring ready transfer of the ambient air through the portal zone to the odor absorbing material.

4. An air freshening and deodorizing system defined in claim 1 wherein said container is defined as being formed from two independent, multi-layered, flexible sheets of material.

5. The air freshening and deodorizing system defined in claim 1, wherein said system further comprises
   E. holding means constructed for retaining the fragrance producing means and being mounted in the holding zone of the container.

6. The air freshening and deodorizing system defined in claim 5, wherein said holding means is further defined as being positioned in the holding zone in cooperative association with the portal zone for assuring ready transfer of the fragrance through the portal zone to the ambient air.

7. An air freshening and deodorizing system for providing controlled, long-term release of an air freshening fragrance and absorption of odors from the ambient air, said system comprising A. a container incorporating a sealed holding zone;
   B. odor absorbing material contained within the holding zone and comprising one or more selected from the group consisting of activated charcoal or active carbon, zeolites, baking soda, silica gel, silica molecular sieves, activated alumina, kieselguhr, fullers earth, and clay minerals;
   C. a portal zone
      a. formed in the container in a normally sealed configuration to prevent the release of the fragrance into the ambient air or the transfer of the ambient air into the holding zone until desired, and
      b. controllably openable to enable the fragrance to be dispersed throughout the ambient air and to allow the air to contact the odor absorbing material while preventing the odor absorbing material or the fragrance bearing carrier from exiting from the holding zone into the ambient surroundings;
   D. a first microporous/permeable membrane layer mounted in the container and positioned between the odor absorbing material and the portal zone of the container for preventing dispersion of the odor absorbing material through the portal; and
   E. fragrance producing means comprising
      a. a highly concentrated, long-lasting, air freshening fragrance comprising a formulation selected from the group consisting of compositions which are unable to be absorbed by the odor absorbing material, and
      b. an inert carrier for holding the fragrance composition and providing controlled release of the fragrance.

8. The air freshening and deodorizing system defined in claim 7, and further comprising a second microporous/permeable membrane layer positioned in juxtaposed spaced relationship with the first membrane layer, with the odor absorbing material sandwiched therebetween.

9. The air freshening and deodorizing system defined in claim 8, wherein said first and second membrane layers are further defined as being bonded together about their outer peripheral surfaces, thereby establishing a retaining zone for sealingly securing the odor absorbing material therein.

10. The air freshening and deodorizing system defined in claim 7, wherein said microporous/permeable membrane is further defined as comprising one or more selected from the group consisting of woven or non-woven, synthetic or natural fibers integrally jointed together, wood pulp, and plastic films or sheets.

11. The air freshening and deodorizing system defined in claim 10, wherein said microporous/permeable membrane is further defined as being formed from a polymeric plastic sheet.

12. The air freshening and deodorizing system defined in claim 11, wherein said polymeric plastic sheet is further defined as comprising one selected from the group consisting of polyurethanes, polyethers, polyesters, polypropylenes, polystyrenes, and combinations thereof.

13. The air freshening and deodorizing system defined in claim 7, wherein said air freshening fragrance composition is further defined as comprising a fragrance derived from one or more botanicals.

14. The air freshening and deodorizing system defined in claim 13, wherein said botanical derived fragrances are further defined as comprising one or more selected from the group consisting of eucalyptus, floral notes, jasmine, lavender, wintergreen, spearmint, wood notes, wormwood, echinacea, lemongrass, calendula, balsam, oleoresins, tea tree, ginseng, licorice, and menthol.

15. The air freshening and deodorizing system defined in claim 7, and further comprising
   F. a second microporous/permeable membrane layer mounted in the container and positioned between the fragrance producing means and the portal of the container for controlling the dispersion of the fragrance to the ambient air.

16. The air freshening and deodorizing system defined in claim 15, and further comprising a third microporous/permeable membrane layer positioned in juxtaposed spaced relationship with the first membrane layer, with the fragrance producing means sandwiched therebetween.

17. The air freshening and deodorizing system defined in claim 16, wherein said second and third membrane layers are further defined as being bonded together about their outer peripheral surfaces, thereby establishing a retaining zone for sealingly securing the fragrance producing means therein.

18. The air freshening and deodorizing system defined in claim 17, wherein said second and third microporous/permeable membranes are further defined as comprising one or more selected from the group consisting of woven or non-woven, synthetic or natural fibers integrally jointed together, wood pulp, and plastic films or sheets.

19. The air freshening and deodorizing system defined in claim 18, wherein said second and third microporous/permeable membranes are further defined as being formed from a polymeric plastic sheet.

20. The air freshening and deodorizing system defined in claim 7, wherein said container is further defined as being formed from two independent multi-layered flexible sheets integrally affixed to each other to form said interior sealed holding zone.

21. The air freshening and deodorizing system defined in claim 20, wherein said independent multi-layered flexible sheets are further defined as comprising A. at least one barrier layer formed from metal foil for preventing transfer of the air freshening/deodorizing composition from the holding zone to the ambient surroundings when the container is sealed, B. at least one low density, linear polyethylene film layer intimately bonded to one surface of the barrier layer for providing inherent strength and surface sealability between the two independent multi-layered, flexible sheets, and C. at least one polyester layer integrally bonded to the opposed surface of the barrier metal foil layer for providing a print receiving surface.

22. The air freshening and deodorizing system defined in claim 7, wherein said container is further defined as being formed from three independent, multi-layered flexible sheets integrally bonded to each other about their respective outer peripheral edges, thereby forming a container having a first and a second separate and independent sealed holding zone and said odor absorbing material is further defined as being contained within the first holding zone and the fragrance producing means is further defined as being contained within the second holding zone.

23. A combined air freshening and deodorizing system for providing controlled, long-term release of an air freshening fragrance and absorption of odors from the ambient air, said system comprising A. a container incorporating a sealed holding zone;

B. odor absorbing material contained within the holding zone and comprising one or more selected from the group consisting of activated charcoal or active carbon, zeolites, baking soda, silica gel, silica molecular sieves, activated alumina, kieselguhr, fullers earth, and clay minerals;

C. fragrance producing means comprising a highly concentrated, long-lasting, air freshening fragrance comprising a formulation selected from the group consisting of compositions which are unable to be absorbed by the odor absorbing material; and D. dispensing means for transferring the odor absorbing means and the fragrance producing means from the sealed holding zone of the container to the ambient air.

24. The combined air freshening and deodorizing system defined in claim 22, wherein said container comprises an aerosol-type container and said dispensing means comprises a propellant.

25. The combined air freshening and deodorizing system defined in claim 24, wherein said system comprises between about 25% and 30% by weight of the air freshening and deodorizing composition and between about 70% and 75% by weight of the propellant.

26. The combined air freshening and deodorizing system defined in claim 24, wherein said air freshening and deodorizing composition is further defined as comprising A. between about 1% and 5% by weight of the total weight of the composition of odor absorbing material;

B. between about 3% and 20% by weight of the total weight of the composition of talc;

C. between about 1% and 10% by weight of the total composition of fragrance producing means; and D. denatured alcohol forming the balance.

27. The combined air freshening and deodorizing system defined in claim 26, wherein said air freshening/deodorizing composition is further defined as comprising one or more compounds selected from the group consisting stearalkonium hectorite, propylene glycol, sorbitan sequioleate, taluaftate, tenoa WL-660, and tenox BHT.

* * * * *